(12) United States Patent
Haindl et al.

(10) Patent No.: US 10,869,970 B2
(45) Date of Patent: Dec. 22, 2020

(54) DIALYSIS NEEDLE

(71) Applicant: B. BRAUN AVITUM AG, Melsungen (DE)

(72) Inventors: Hans Haindl, Wennigsen (DE); Kevin Woehr, Felsberg (DE)

(73) Assignee: B. BRAUN AVITUM AG, Melsungen (DE)

( * ) Notice: Subject to any disclaimer, the term of this patent is extended or adjusted under 35 U.S.C. 154(b) by 194 days.

(21) Appl. No.: 15/743,453

(22) PCT Filed: Jul. 18, 2016

(86) PCT No.: PCT/EP2016/067044
§ 371 (c)(1),
(2) Date: Jan. 10, 2018

(87) PCT Pub. No.: WO2017/009483
PCT Pub. Date: Jan. 19, 2017

(65) Prior Publication Data
US 2018/0200454 A1 Jul. 19, 2018

(30) Foreign Application Priority Data
Jul. 16, 2015 (DE) ............. 10 2015 009 190

(51) Int. Cl.
*A61M 5/32* (2006.01)
*A61M 1/36* (2006.01)
(Continued)

(52) U.S. Cl.
CPC ........ *A61M 5/3221* (2013.01); *A61M 1/1654* (2013.01); *A61M 1/3656* (2014.02);
(Continued)

(58) Field of Classification Search
CPC .. A61M 1/3656; A61M 1/3661; A61M 5/158; A61M 5/3221; A61M 2005/1586;
(Continued)

(56) References Cited

U.S. PATENT DOCUMENTS

| 4,929,241 A | 5/1990 | Kulli |
| 6,443,929 B1 * | 9/2002 | Kuracina ........... A61B 5/15003 604/192 |

(Continued)

FOREIGN PATENT DOCUMENTS

| CN | 104771807 A | 7/2015 |
| DE | 19953068 A1 | 6/2001 |

(Continued)

OTHER PUBLICATIONS

German Office Action for German Application No. 10 2015 009 190.5, with partial translation, dated Apr. 5, 2016—15 Pages.
(Continued)

*Primary Examiner* — Brandy S Lee
*Assistant Examiner* — Nidah M Hussain

(57) ABSTRACT

A safety needle is disclosed having a puncture needle with a needle lumen and a ground tip; a holding device that, during use, bears on the skin of a patient and holds the puncture needle; and a safety mechanism with a protection element that has a first, opened state and a second, closed state. When the holding device is taken away from the skin and/or when the holding device is moved with respect to the defined position, the safety mechanism automatically moves the protection element from a first position, in which the tip of the needle is exposed, to a second position, in which the tip of the needle is covered as the protection element at the same time transfers automatically from the first, opened state to the second, closed state.

24 Claims, 26 Drawing Sheets

(51) Int. Cl.
*A61M 39/22* (2006.01)
*A61M 5/158* (2006.01)
*A61M 1/16* (2006.01)
*A61B 17/34* (2006.01)
*A61M 39/10* (2006.01)

(52) U.S. Cl.
CPC .......... *A61M 1/3661* (2014.02); *A61M 5/158* (2013.01); *A61M 39/22* (2013.01); *A61B 17/3494* (2013.01); *A61M 2005/1586* (2013.01); *A61M 2005/3254* (2013.01); *A61M 2039/1005* (2013.01); *A61M 2039/224* (2013.01); *A61M 2205/0244* (2013.01); *A61M 2205/13* (2013.01); *A61M 2205/18* (2013.01)

(58) Field of Classification Search
CPC ...... A61M 2005/3254; A61M 25/0612; A61M 25/0618; A61M 25/0625; A61M 25/0631; A61M 25/0637
USPC .......................................................... 604/198
See application file for complete search history.

(56) References Cited

U.S. PATENT DOCUMENTS

| | | | |
|---|---|---|---|
| 9,687,633 B2 | 6/2017 | Teoh | |
| 2002/0004650 A1 | 1/2002 | Kuracina et al. | |
| 2002/0161333 A1* | 10/2002 | Luther | A61M 39/284 604/167.01 |
| 2002/0161338 A1* | 10/2002 | Peterson | A61M 25/0618 604/198 |
| 2006/0130591 A1 | 6/2006 | Perkins | |
| 2009/0259201 A1* | 10/2009 | Hwang | A61B 5/15003 604/263 |
| 2010/0042118 A1* | 2/2010 | Garrison | A61M 25/04 606/148 |
| 2010/0063455 A1 | 3/2010 | Moyer et al. | |
| 2012/0078096 A1* | 3/2012 | Krolik | A61M 25/1011 600/435 |
| 2012/0220956 A1* | 8/2012 | Kuracina | A61M 5/3273 604/263 |
| 2014/0309687 A1* | 10/2014 | Atkinson | A61M 25/02 606/218 |
| 2014/0336582 A1* | 11/2014 | Tisci | A61M 25/0097 604/164.08 |
| 2015/0112281 A1 | 4/2015 | Haindl | |
| 2015/0151086 A1 | 6/2015 | Teoh | |
| 2015/0224285 A1* | 8/2015 | Howell | A61M 25/02 604/180 |
| 2016/0015941 A1* | 1/2016 | Tanabe | A61M 25/0606 604/164.08 |
| 2019/0366070 A1* | 12/2019 | Kume | A61M 1/3659 |

FOREIGN PATENT DOCUMENTS

| | | |
|---|---|---|
| DE | 102012206557 A1 | 10/2013 |
| DE | 102009004018 B4 | 2/2014 |
| EP | 1985324 A1 | 10/2008 |
| EP | 2042206 B1 | 4/2011 |
| WO | 9924145 A1 | 5/1999 |

OTHER PUBLICATIONS

International Search Report and Written Opinion for International Application No. PCT/EP2016/067044, dated Oct. 25, 2016—12 Pages.

European Search Report for European Application No. 18 183 192.6, dated Sep. 17, 2018, with translation, 8 pages.

Chinese Office Action for Chinese Application No. 201680041883.8, dated Mar. 2, 2020, with translation, 16 pages.

* cited by examiner

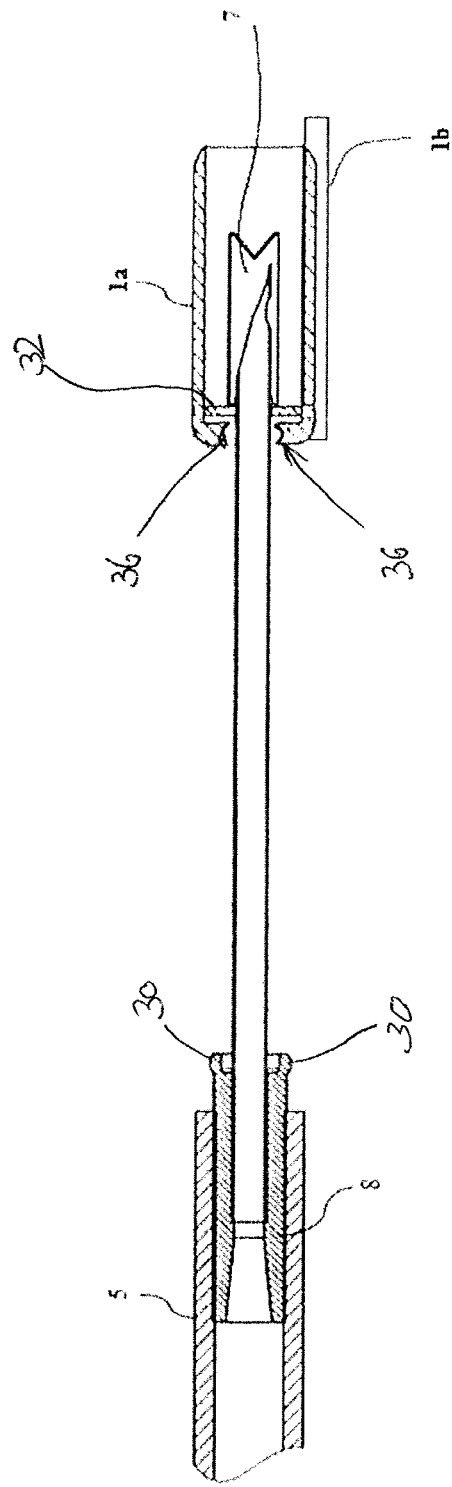

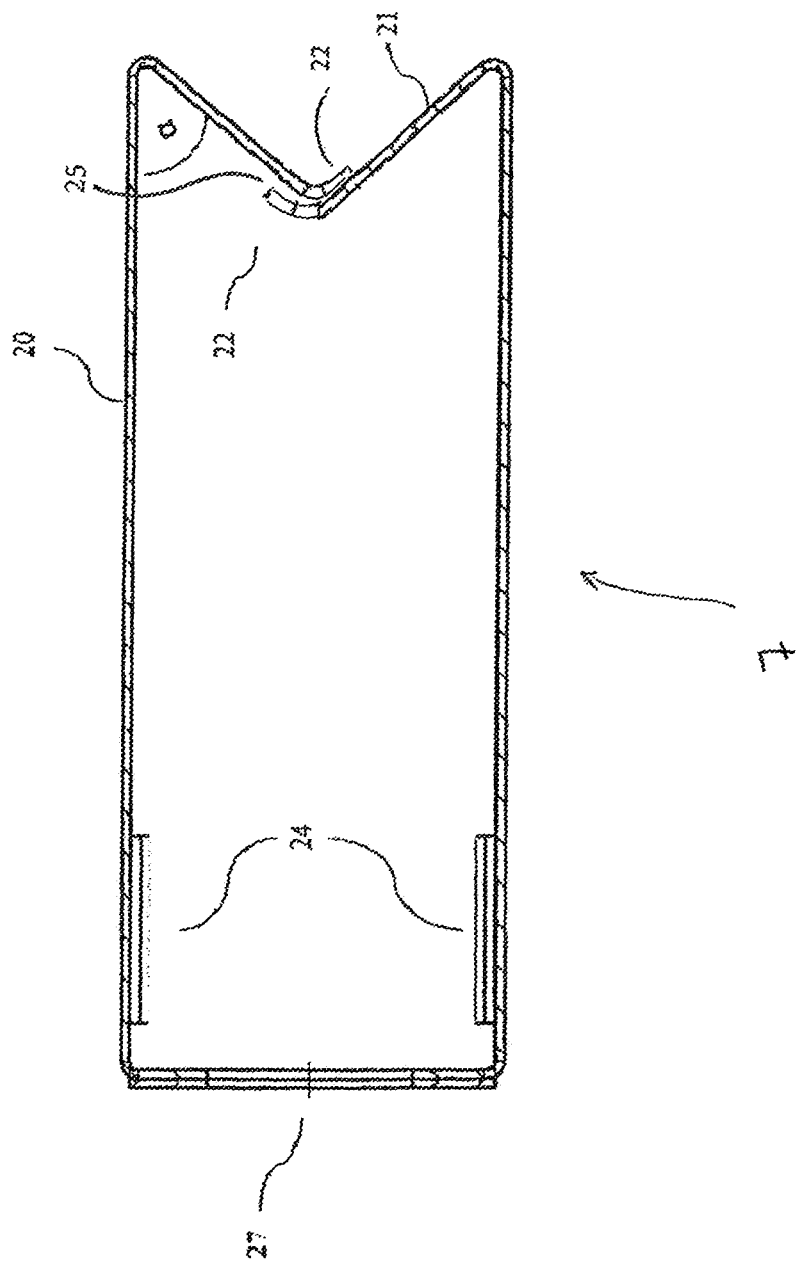

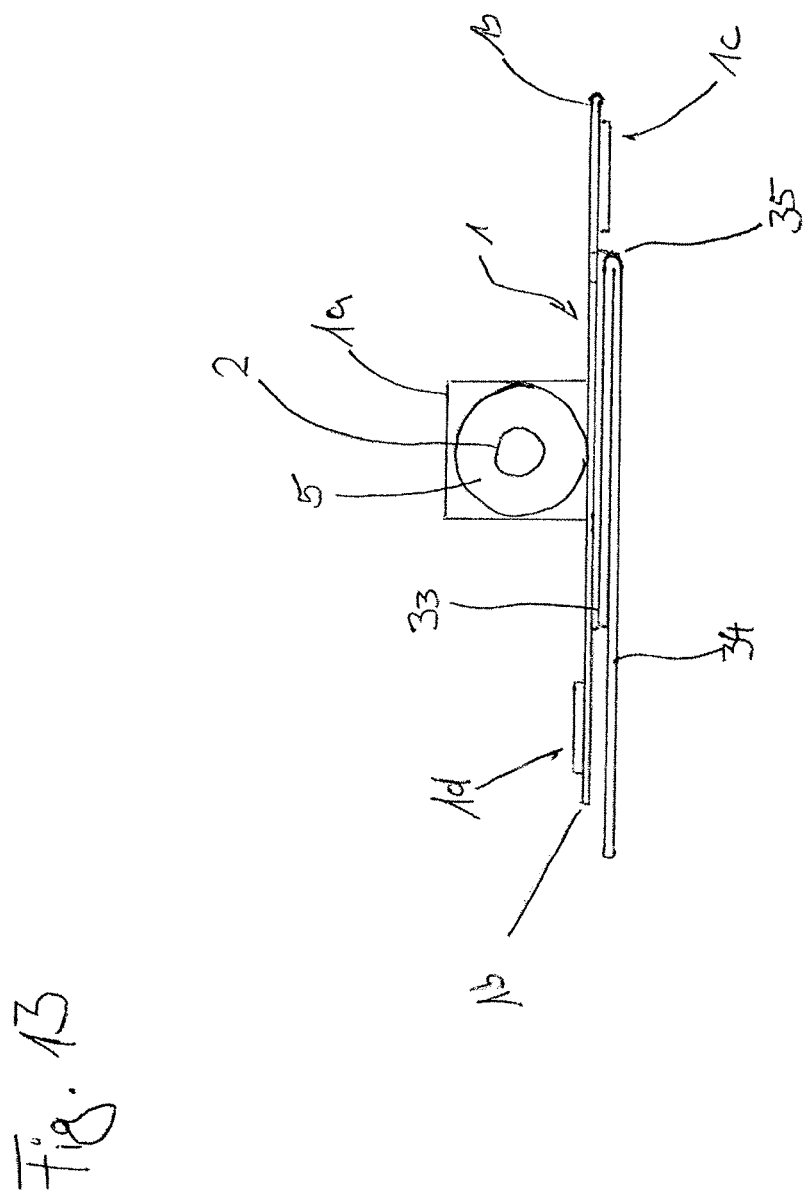

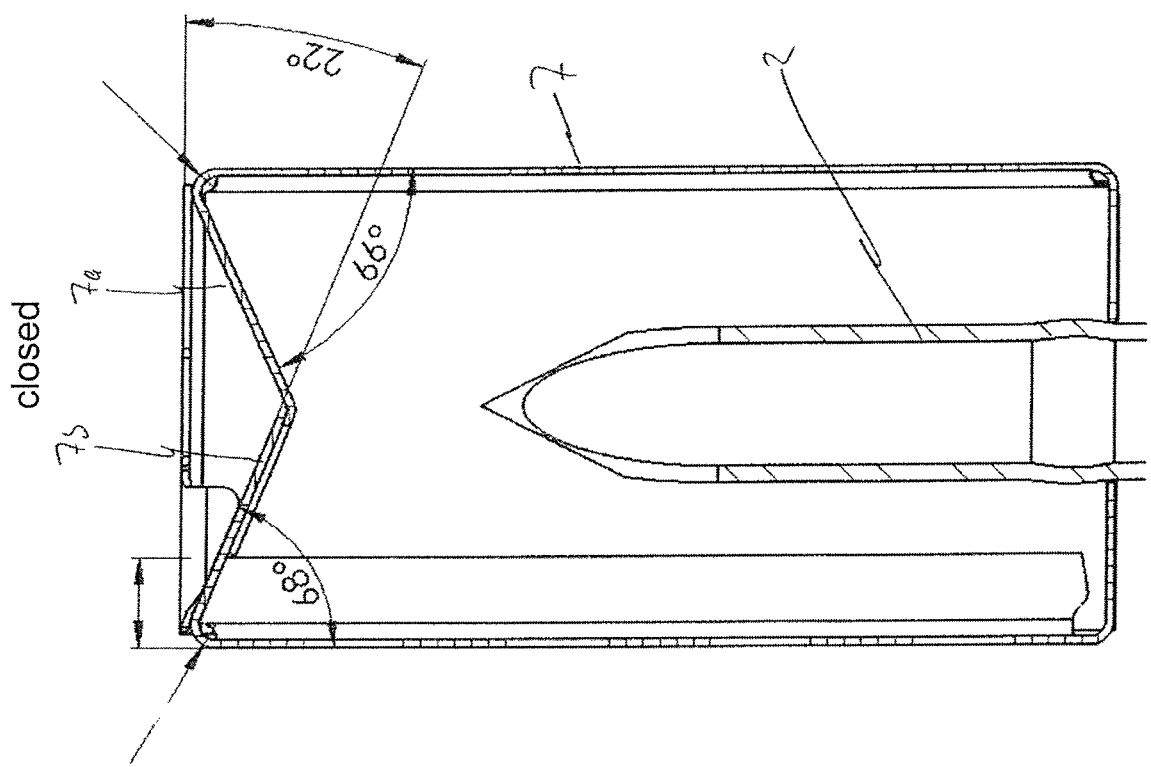

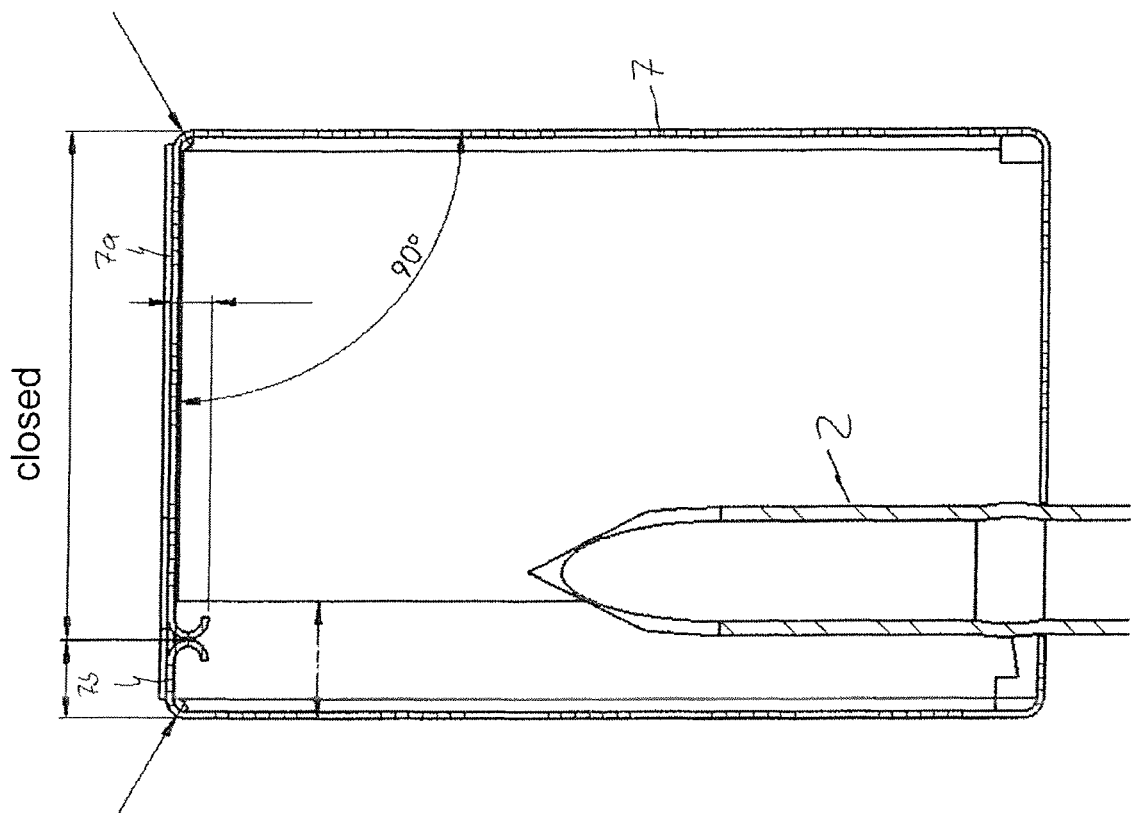

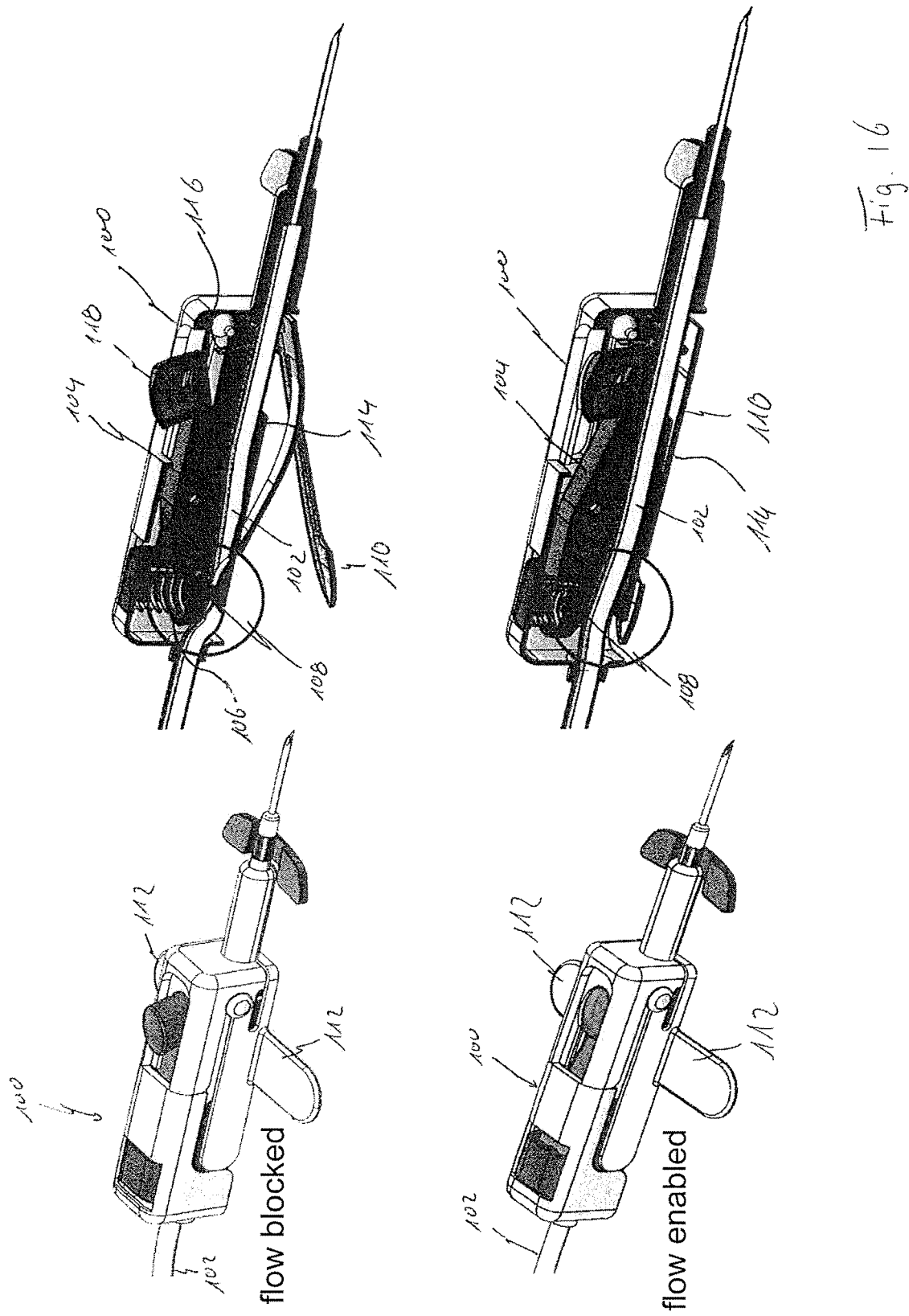

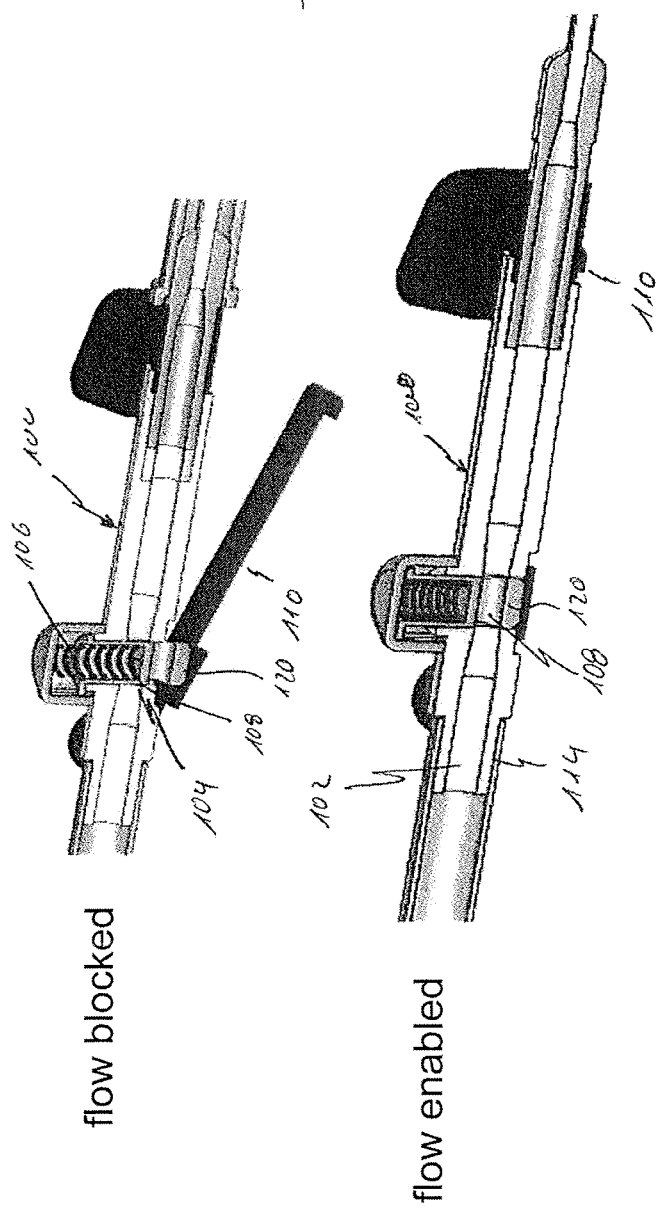

DIALYSIS NEEDLE

CROSS REFERENCE TO RELATED APPLICATIONS

This application is the U.S. national phase application of PCT International Application No. PCT/EP2016/067044 filed Jul. 18, 2016, which claims priority to German Patent Application No. DE 10 2015 009 190.5 filed Jul. 16, 2015, the contents of each application being incorporated by reference herein.

FIELD OF THE INVENTION

The present application relates to a safety needle for the extracorporeal blood treatment such as for dialysis, for example, and in particular to a dialysis needle or fistula needle.

BACKGROUND OF THE INVENTION

The accident prevention regulation TRBA 250 requires that in all medical workplaces where the handling of needles poses a risk of injury for users, safety needles are used where available which after use are actively or passively protected such that the users or third parties cannot be injured any more. This requirement applies, among other things, also for dialysis wards and dialysis centers. In dialysis, a vessel artificially placed under the skin, a so-called shunt, is punctured mostly with two needles. These needles have a large lumen and therefore contain relatively large amounts of blood, so that in the event of a user getting injured with these needles the risk of infection is to be rated extremely high. What is more, the frequency of blood-borne infections such as hepatitis B and C as well as HIV is significantly higher for dialysis patients than for the average population.

In order to reduce the risk of infection, so-called safety needles have already been proposed for dialysis. The principle of these safety needles is based on the fact that the needle, after its use but prior to removing the needle attachment affixed to the skin of the patient, is removed from the blood vessel by pulling the needle's hose attachment and is drawn into the needle attachment where the needle latches in place, so that the needle tip cannot come out of the needle attachment again.

Unfortunately, there have been some severe incidences with these safety needles which have arisen because the hose on the needle has not been separately fastened to the skin of the patient with a patch, as required by the manufacturer. This is why e.g. a movement of the patient could apply tensile forces on the hose which could result in the needle retracting into its protective device during dialysis. This means that the venous needle does not return the blood from the dialysis machine back to the patient, but into the surroundings. Since the outflow of the blood is not hindered and hence there is no pressure increase in the venous hose branch, which is also referred to as the venous side, the dialysis machine continues pumping without issuing an alarm. This may result in a patient bleeding to death.

The incidences which occurred with safety needles underline a problem in dialysis which has been existing from the very beginning and has not been solved until today. This is the safety monitoring of the venous branch of the dialysis. The dialysis machines are provided with sensible sensors perceiving disturbances in the dialysis procedure and, if required, switching off the machine and/or issuing an alarm. If the arterial needle slips out, for instance, the needle will not be able to draw in blood any more as long as the needle tip is still in the tissue, and there will be an underpressure in the arterial hose branch which is also referred to as the arterial side. The dialysis machine will take notice of this situation, switches off and issues an alarm. If the arterial needle slips out of the tissue completely, it draws air instead of blood. This is immediately detected in the machine e.g. by an ultrasound air detector, the machine switches off and issues an alarm. In this respect, the arterial branch is automatically monitored.

For the venous hose branch, the situation is a different one. If the venous needle gets out of place and has its tip positioned in the tissue, i.e. between the shunt and the skin, it will be completely ejected from the tissue at once due to the pumped flow of blood, and the blood flow drains into the surroundings. The occurring pressure variations are usually so small and short-termed that the pressure sensor of the dialysis apparatus cannot perceive them in most cases. This is why the slipping out of venous needles has already resulted in numerous deaths by dialysis patients bleeding out. With the feed rates employed, the patient may be dead after three to five minutes.

DESCRIPTION OF THE RELATED ART

The prior art describes various methods and devices with which the correct fit of a needle can be monitored, see, e.g., DE 10 2009 004 018 A1, US 2006/0130591 A1, DE 199 53 068 A1 and WO 99/24145. These methods and devices, however, are extremely complex and involve in particular a special sensor system. Accordingly, these known methods and devices are expensive and not very practicable.

Further, DE 10 2012 206 557 A1 discloses a safety needle comprising a safety mechanism which is suitable to automatically retract the puncture needle to a protected position in the housing when the needle housing is removed from the skin of the patient. A distal opening of the needle housing can be partially covered with a cover element in order to bring about an inhibition of the blood flow causing a pressure increase that can be realized by a dialysis apparatus. However, the safety mechanism actively moves the needle with this safety needle, which may be disadvantageous insofar as it might be pulled out of the blood vessel even if it was in proper position therein. Moreover, the closure mechanism using the additional cover element is relatively complicated as it requires, on the one hand, a mechanism for protecting the needle and, on the other, a mechanism for generating the blood stasis.

SUMMARY OF THE INVENTION

It is thus an object of the present invention to provide a safety needle which accounts for the above-mentioned safety requirements in a simple, but nevertheless reliable manner. It is a further object of the present invention to provide a safety needle which can be produced at low cost and has an easy handling.

These and further objects are achieved with a safety needle according to the independent claim. Further preferred features are described in the dependent claims.

Accordingly, the present invention provides a safety needle, a holding device and a safety mechanism. The puncture needle comprises a needle lumen and a preferably ground tip. The holding device is suitable, during use, for bearing in a defined position on the skin of a patient and for holding the puncture needle. The safety mechanism comprises a protection element which can adopt a first, opened state and a second, closed state. The safety mechanism is preferably such that, when the holding device is taken away from the skin and/or is moved with respect to the defined position, it automatically moves the protection element from a first position, in which the tip of the needle is exposed, to a second position, in which the tip of the needle is covered, as a result of which the protection element at the same time transfers automatically or in self-activating manner from the first, opened state to the second, closed state. It is preferred that the safety mechanism, during removing the holding device from the skin and/or moving the holding device with respect to the defined position, is automatically activated in the first position, i.e. brought into a state in which the protection element can move from the first to the second position, provided that such movement is not hindered due to the fact that the needle tip is still in the vessel. As soon as the needle slips out of the vessel and the tip of the needle is exposed, the protection element moves preferably automatically to the second position in which the tip of the needle is covered. Thus, the risk of getting injured by the needle tip is effectively minimized without the safety mechanism according to aspects of the invention unintentionally causing the extraction of the needle out of the vessel.

Stated in other words, the safety needle according to aspects of the invention is preferably designed such that the needle cannot come loose from the patient with an opened tip, since a detachment of the holding device from the skin and/or a movement of the holding device with respect to the defined position safeguards the puncture needle together with the ground tip. In this context, it is preferred that the needle is not actively moved by the safety mechanism. Rather, the process of securing is preferably achieved in that the protection element is moved from the first position to the second position. This is particularly advantageous if the safety mechanism is not triggered by detaching the holding device from the skin, but by a movement of the holding device with respect to the defined position, as an active retraction of the needle would possibly be not required at all as long as the needle tip is still in the vessel.

In yet other words, the present invention according to an aspect optionally to be claimed independently relates to a puncture needle, a holding device and a safety mechanism, which in combination form a safety needle according to aspects of the invention. The safety mechanism is adapted to keep the tip of the puncture needle exposed in a first, opened state (first latching position) and to be moved relative to the puncture needle in a second, closed state (e.g. using a spring), in which the tip of the puncture needle is shielded/covered toward the surroundings and preferably closed at least in parts toward the surroundings (second latching position).

Furthermore, the safety mechanism and the holding device are matched with each other such (in constructional terms) that any detachment of the holding device from the patient's skin and/or any movement/displacement of the holding device with respect to a defined position on the patient's skin transfers the safety mechanism to a triggered or armed intermediate state in which its movement mechanism is put in operation to transfer the safety mechanism from the first state to the second state (the latter coming into effect not until the puncture needle is actively pulled out of the patient's blood vessel which acts, so to speak, as an abutment.

In a preferred embodiment, the safety mechanism comprises a protection element moving device (movement mechanism) with which the protection element can be moved from the first to the second position. This protection element moving device is preferably arranged to be proximal relative to the protection element. The protection element moving device preferably comprises a first spring and a retaining wall or retaining ring. It is preferred that the protection element is not connected to the housing of the holding device, preferably not by a material bond.

Basically, the present invention is of importance for all those needles which comprise a housing or a holding device that is temporarily brought into contact with the skin of a patient. However, the safety needle of the present invention is especially suitable for an extracorporeal blood treatment. A particularly preferred field of application is the dialysis because of the reasons set out above.

In the event of a dialysis or another extracorporeal blood treatment, the safety needle of the present invention is particularly advantageous, as the protection element of the safety mechanism does not impede the flow of blood through the needle in the second, closed state. This results in a pressure increase in the venous hose branch, which can be detected for instance by a dialysis machine, so that it switches off automatically. According to aspects of the invention, no additional cover element is required here (in contrast to DE 10 2012 206 557 A1), which would close a housing opening, but the protection element itself can be folded open or closed. In other words, the protection element comprises a wall defining a housing-like structure, in which the closed state is achieved exclusively by elements of the wall. This can be achieved, for instance, in that the protection element comprises two half shells which can be unfolded or folded. As an alternative, the protection element may have two lateral wall portions which can be moved contrary to a spring force towards outside such that the opened state is obtained. Preferably, these lateral wall portions are formed to be elastic and have their distal end provided with a distal wall portion. As an alternative, also four lateral wall portions may be formed to be elastic which all spring toward each other in order to form the closed state.

The protection element preferably comprises two resilient arms which close the protection element in the second state. These two resilient arms preferably form two side walls of a housing formed by the protection element, as described above. Here, the arms are preferably formed such that they can slide along the outer side of the needle with low friction in the first state.

Stated in other words, the safety mechanism according to aspects of the invention preferably comprises a protection element in the form of a sleeve, housing or clamp, whose distal end portion is designed in the form of at least one (preferably two) elastically preloaded door wing(s) which is/are pushed open by the puncture needle in radial direction and automatically closed upon a relative movement in distal direction beyond the tip of the needle.

Preferably, at least one of the arms/door wings has its distal end provided with an arresting device which prevents the protection element from being moved from the second position to the first position. Here, the arresting device preferably may have a bent portion of the arm and/or a barb. The bent portion of the arm preferably forms a part of a distal wall of the housing formed by the protection element. It is preferred here that the bent portion of the arm and the distal wall of the protection element point in the radial direction as well as in the proximal direction. In other words, the angle between the bent portion of the arm and the remainder of the arm preferably amounts to less than 90°, more preferably less than 80°, even more preferably less than 70° and most preferably less than 60°. Such an acute angle has several advantages. On the one hand, such an acute angle facilitates the process in which the arms slide along the outer side of the needle in distal direction. On the other hand, such an acute angle may serve as an arresting device, because the needle tip comes into engagement with the bent portion of the arm or gets entangled with it upon the attempt to retract the protection element from the needle in proximal direction.

Instead of such bent arms, the distal end of the protection element may also be formed to be concave in some other way. Generally speaking, the above-mentioned advantages are achieved even if the distal wall portion is bulged proximally or extends in a somewhat different manner in proximal direction, i.e. if the distal end of the protection element protrudes into the interior of the protection element.

It is further preferred that the two arms/door wings are formed such that they come into engagement with each other (at their free terminal edges), preferably get latched and/or entangled with each other, if the protection element is in the second, closed position. To this end, the two arms preferably have hook elements or curved zones which come into engagement or get entangled with each other in the second position. This can prevent that the two arms can be pushed apart by the pressure of the blood.

Further, there is the possibility to design one of the two arms/door wings so as to be narrower/shorter than the other, opposite arm/door wing; furthermore, a pivot/end stop can be formed on the housing-shaped protection element for both arms/door wings. With such a constructional configuration, any shifting movement of the housing-shaped protection element relative to the puncture needle beyond the tip thereof causes a pivoting of the narrower/shorter arm to the closed position and then (with a temporal offset) a pivoting of the wider/longer arm, so that in the closed position the two arms arrange on top of each other in a sealing manner while being supported by the end stop.

Preferably, the protection element consists of an elastomer or is coated with an elastomer at least in parts, with the elastomer preferably comprising one material or any combination of the following materials: silicone, polyurethane, PTFE. An elastomer of this type improves the sealing between the individual portions of the protection element, i.e. between the two half shells or the lateral walls of the protection element. If the protection element has two resilient arms, it is particularly preferred that at least the side edges of these resilient arms are provided with the mentioned elastomer. As an alternative, the protection element comprises a metal, preferably stainless steel, preferably in the form of a sheet metal, and preferably it consists thereof.

The inner side of the protection element is preferably coated with a coagulatory material at least in parts, wherein the coagulatory material preferably one of or any combination of the following materials: proteins such as collagen, fibrin, thrombin; polypeptides such as gelatin; polysaccharides such as cellulose, sugars;

glucosamines such as chitosan; alginates; adsorbing substances such as zeolite, aluminophosphate; denaturing substances such as aldehydes, alum, aluminum salts. Such a coating has the advantage that the blood flow is additionally impeded or suppressed after the triggering of the safety mechanism. During use of the safety needle, the blood flows only through the needle lumen. However, if the needle tip is inadvertently removed from the vein of the patient, so that the safety mechanism is triggered and the protection element is moved to the second position in which the tip of the needle is covered, the dialysis machine pumps blood into in the interior of the protection element. If this blood coagulates due to the coagulatory material on the inner side of the protection element, the flow resistance is significantly increased so that a pressure increase which can be detected by the dialysis apparatus can occur within a shorter time.

A similar effect may be achieved in that the protection element has the inner side provided with any material or any combination of the following materials: elastic foamed plastic such as a foamed plastic made of polyurethane or silicone; swelling agents; spongy and/or water-absorbing substances. By way of example, an elastic foamed plastic provided in the interior of the protection element may fill up the interior space essentially to the full extent during closing the protection element, so that any blood flow can be effectively prevented. In case swelling agents are provided on the inner side of the protection element, these will swell as soon as they come into contact with blood, and then likewise fill up the interior space of the protection element essentially to the full extent in order to represent an effective barrier for the blood flow.

It is preferred that the needle comprises one, two or more protrusions preventing the protection element from becoming detached from the needle. If the safety mechanism according to aspects of the invention is activated, blood from the dialysis apparatus is pumped into the interior of the protection element in the event of a dialysis. In case the protection element would become detached from the needle tip due to the pressure generated thereby, the safety mechanism would be virtually without any effect. This is why it is preferred to prevent such a detachment with one or more protrusions. It goes without saying that the needle may also have some other means for blocking the protection element against a shifting in distal direction.

By way of example, the distal end of the needle may also be provided with one or more widened zones or a groove instead of protrusions, in which the protection element latches in place. As an alternative or in addition, the protection element may also be connected to the needle attachment (or a proximal portion of the needle) by a connecting element such as a thread. In this case, the thread preferably has a length which prevents that the housing-type or clamp-like protection element is completely stripped off from the needle tip.

It is preferred that the two or more protrusions are arranged at the same position as seen in axial direction. It is preferred that at least two, preferably exactly two protrusions are arranged at the same position as seen in axial direction. As an alternative, the two or more protrusions are preferably arranged at different positions as seen in axial direction. It is preferred that the one, the two or the several protrusions are produced by a preferably mechanical crimping process.

The holding device is preferably provided with a detachable means for preventing the triggering of the safety mechanism before use of the safety needle. This may preferably be an adhesive strip and/or a detachable clip and/or hand grip.

In a preferred embodiment, the holding device comprises an adhesive strip on the side facing the skin of the patient, i.e. on the side facing away from the housing of the safety device. Before use, the adhesive strip is at least partially, preferably fully covered with a cover preferably made of paper, preferably until the needle has reached its desired position in the vein. This cover ensures a trouble-free insertion of the needle into the veins, i.e. any unintentional adherence of the holding device on the skin of the patient or the gloves of the user is prevented thereby. It is preferred that the cover preferably made of paper is folded such that the cover is folded and projects beyond the adhesive strip. This ensures that it can be gripped well and peeled off. Subsequently, the holding device can be affixed to the skin of the patient with a slight downward pressure. Thus, the holding device is fixed not until the safety needle has been placed in the correct position. After completion of the dialysis procedure, a swab is pressed against the puncture site and the needle is withdrawn.

In a preferred embodiment, a connecting element/coupling between the housing of the holding device, in which the safety mechanism is supported, and a hose is formed so as to be disconnectable. In this case the user can pull the hose and retract the needle from the vein. In this process, the protection element is positioned distally at the tip of the needle and encompasses it at the distal end. Subsequently, the holding device can be grasped preferably at its wings and peeled off from the skin of the patient with a pull which is preferably perpendicular to the needle axis and then can be safely disposed, as the tip of the safety needle is surrounded by the protection element. The protection element has not been triggered in this case, but is still in the housing of the holding device.

If the needle is unintentionally removed during the treatment, for instance by a proximal movement of the hose, the disconnection of the connecting element from the housing of the holding device likewise results in the protection element being moved to the second state, i.e. to the protected position. It is thus achieved that the user is protected against pinprick injuries and, due to the increased flow resistance, a pressure increase within the apparatus for treating an extracorporeal blood exchange is detected and the blood flow is stopped.

It is preferred that the safety mechanism comprises a first spring which is preferably arranged proximal with regard to the protection element and with which the protection element can be moved from the first to the second position. Regarding the holding device and/or the safety mechanism, the protection element is thus moved distally from the first state (stand-by position) to the second state (protected position). More specifically, it is only the first spring alone which moves the protection element. It is preferred that the present safety needle does not have any further protection element which is not actuatable by the first spring. It is preferred that the first spring is arranged in the stand-by position at the proximal end of the safety mechanism, i.e. in the first state.

Said first spring preferably is a coil spring. It is further preferred that the safety mechanism comprises a second spring (latching spring) which is suitable to automatically relax and thus release the first spring (i.e. abandoning the first latching position and arming the safety mechanism) when the holding device is taken away from the skin and/or is moved with respect to the defined position. The second spring preferably is a leaf spring or a conical coil spring. As an alternative or in addition thereto, the second spring preferably comprises one or more latching hooks directly or indirectly coming into engagement with the first spring.

According to aspects of the invention, the second, closed state does not necessarily have to represent a completely closed state. Rather, the protection element may comprise at least one or more gaps and/or openings in the second state. In that case, however, it will be preferred that the flow resistance of human blood through all the gaps and/or openings is larger than the flow resistance through the needle lumen. This has the effect that the blood flow is impeded if the safety mechanism is triggered, resulting in a detectable increase of the pressure, so that a for instance dialysis apparatus may automatically switch off. To this end, it is also preferred that the sum of the cross-sectional areas of all gaps and/or openings is smaller than the cross-sectional area of the needle lumen. It is further preferred that the flow resistance of human blood through all gaps and/or openings is larger than the flow resistance through the needle lumen by such an amount that maintaining a constant blood flow of between 300 ml/min and 600 ml/min requires a pressure increase of at least 10 mmHg, preferably at least 30 mmHg and particularly preferred of at least 50 mmHg.

It is preferred that the holding device comprises a connection piece for a hose or is integrally connected to a hose. It is preferred that the needle together with the hose is rotatably supported in the holding device.

The safety needle according to aspects of the invention can be produced in a simple manner and at low cost, ensures a high safety level in terms of injuries and solves the above mentioned problems in the context with dialysis needles.

According to a further aspect optionally capable of being claimed independently, the present invention finally relates to the provision of a blood stopping means capable of forming a (mechanically rigid) unit preferably with a safety needle in particular according to aspects of the present invention, comprising a clamping/pinching body which is biased against a flexible hose (with a spring) and a release lever or release button (supported on/in the housing of the blood stopping means) which is in operative engagement or can be brought into operative engagement with the clamping/pinching body and is arranged such that upon or by placing the blood stopping means (its housing) on a surface, preferably the skin of a patient, it is moved to a first position (by pressing the housing against the surface) in which the clamping/pinching body is spaced from the hose, and upon lifting the clamping/pinching body from the surface automatically (due to a spring preload) moves to a second position in which the clamping/pinching body comes in squeezing engagement with the hose (and blocks it).

BRIEF DESCRIPTION OF THE DRAWINGS

The invention is best understood from the following detailed description when read in connection with the accompanying drawings.

FIGS. 6A, 6B are lateral sectional views of the safety needle according to FIGS. 5A, 5B, but in the second latching position;

FIG. 12A is a lateral sectional view of a protection element according to a further preferred embodiment;

FIG. 13 shows a cross-section through the puncture needle and the holding device of the safety needle according to aspects of the invention;

FIGS. 15A, 15B each show a lateral sectional view of a protection element according to a further preferred embodiment in the first and the second latching position;

FIG. 16 is a lateral sectional view of an (additional) hose clamp according to a first preferred embodiment of the present invention;

FIG. 17 is a lateral sectional view of an (additional) hose clamp according to a second preferred embodiment of the present invention and FIGS. 18A and 18B show a duckbill valve for being installed/arranged on the housing of the holding device accommodating the safety mechanism.

DETAILED DESCRIPTION OF THE PREFERRED EMBODIMENTS

Figure 1:
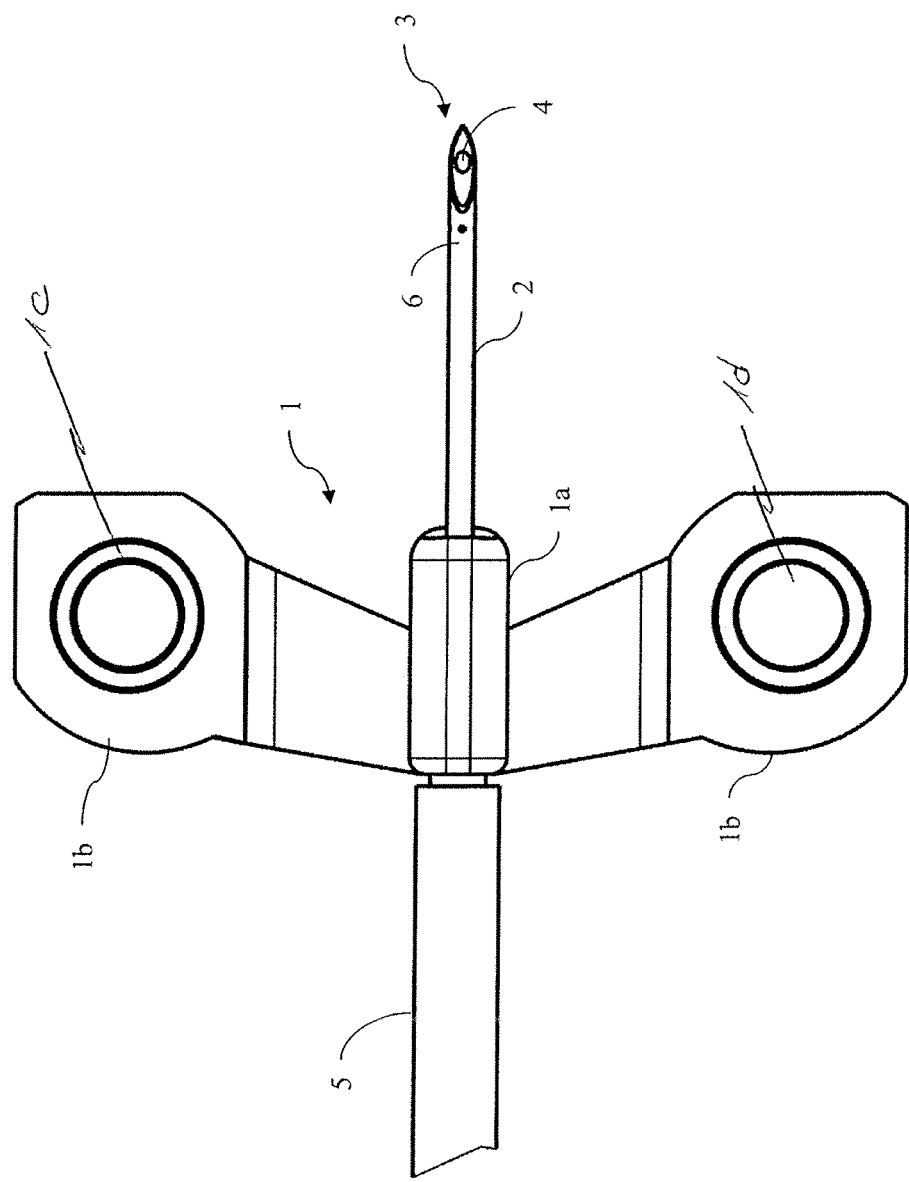
FIG. 1 is a top view of a safety needle according to a preferred embodiment with the protection element being in the first position.
Figure 2:
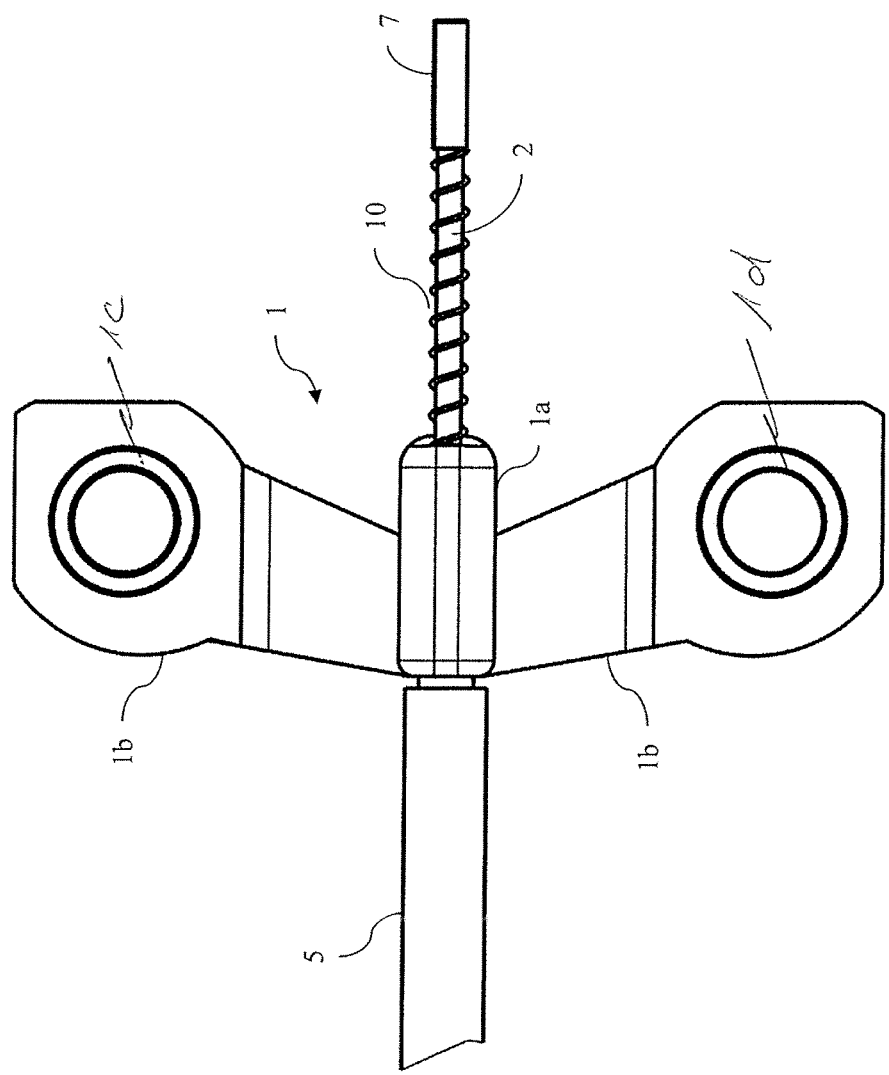
FIG. 2 is a top view of the safety needle of FIG. 1 with the protection element being in the second position.
Figure 3:
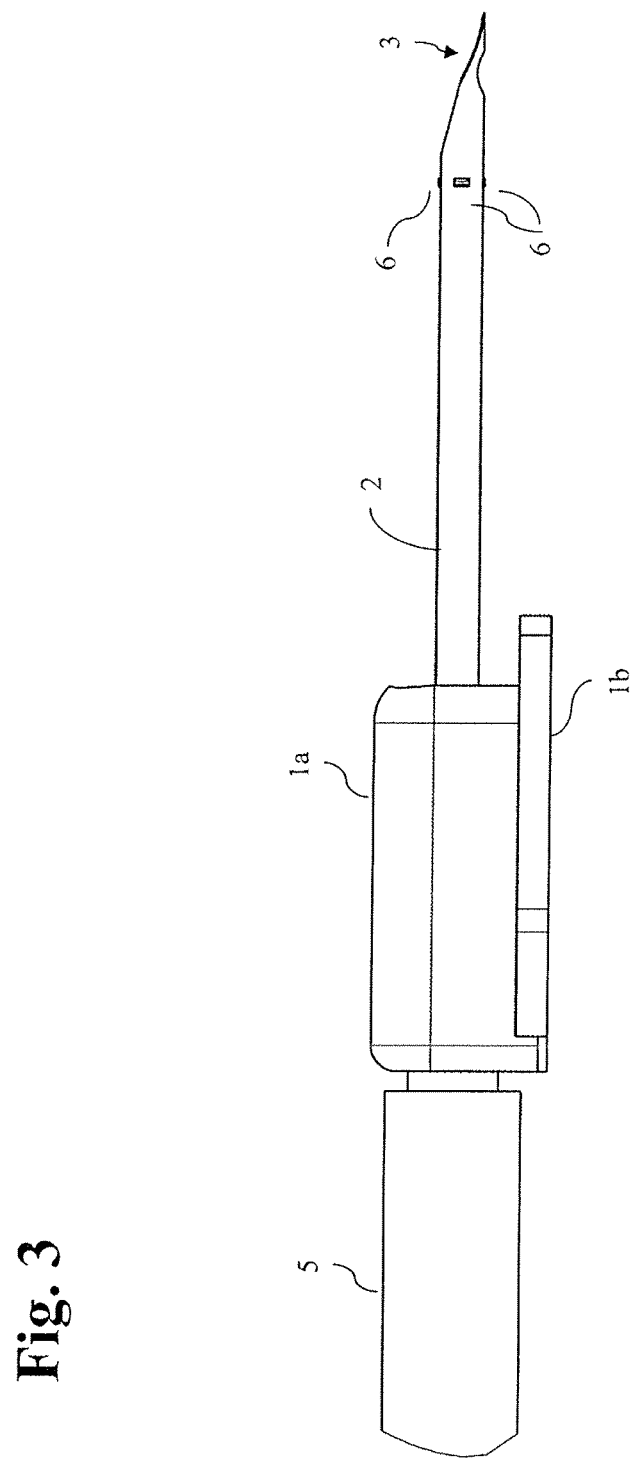
FIG. 3 is a side view of the safety needle according to FIG. 1.
Figure 4:
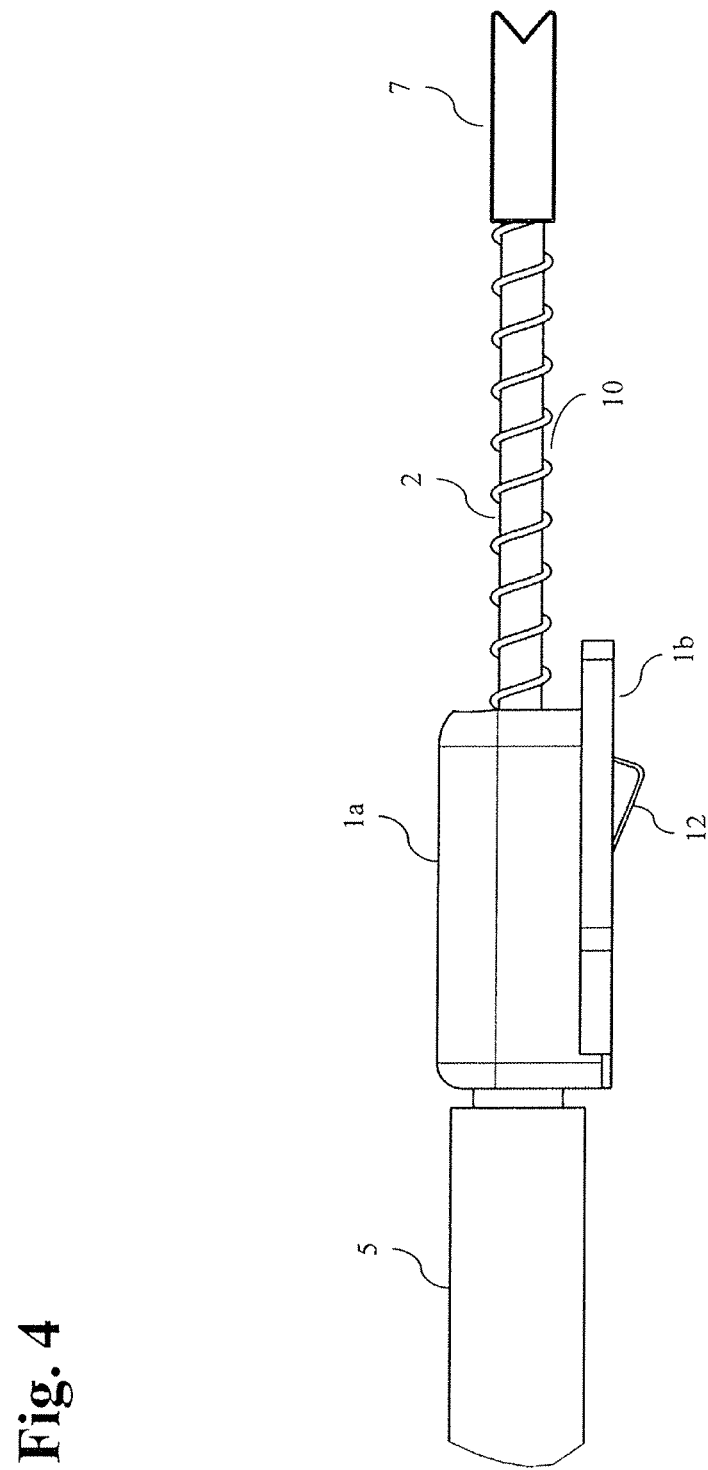
FIG. 4 is a side view of the safety needle according to FIG. 2.
Figure 5:
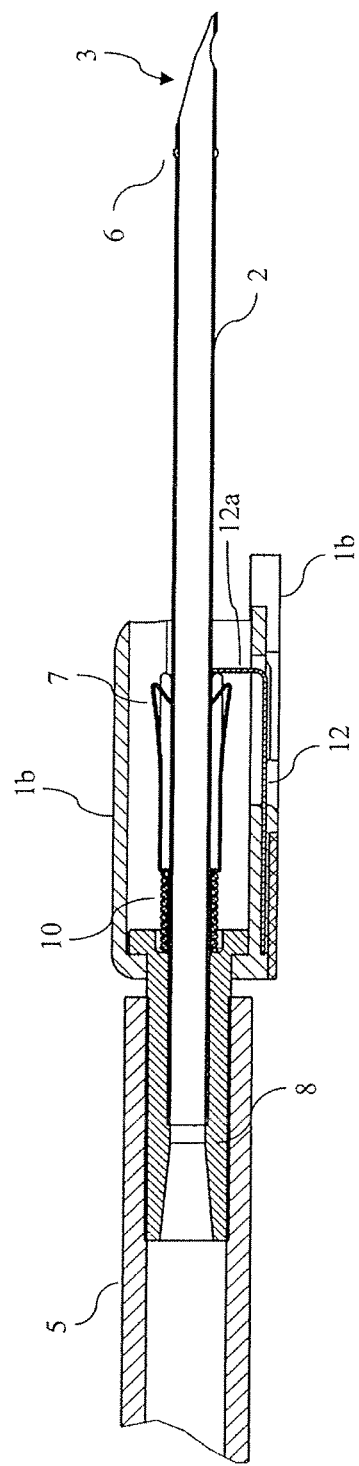
FIG. 5 is a lateral sectional view of the safety needle according to FIG. 1.
Figure 6:
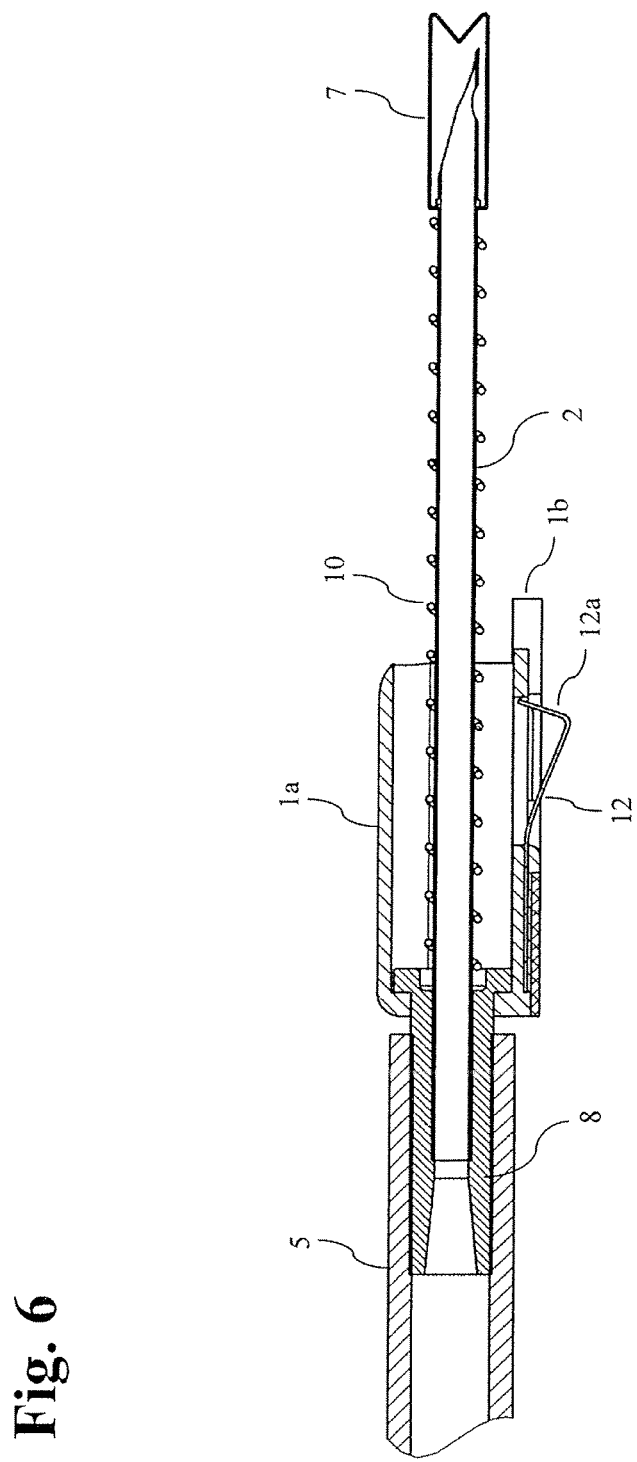
FIG. 6 is a lateral sectional view of the safety needle according to FIG. 2.

FIGS. 1 to 6 show different views of a safety needle according to a preferred embodiment of the present invention, wherein the protection element is in the first position in FIGS. 1, 3 and 5 and in the second position in FIGS. 2, 4 and 6. The safety needle comprises a puncture needle 2 having a needle lumen 4 and a ground tip 3. The puncture needle 2 is connected to a hose 5. The safety needle further comprises a holding device 1 which is suitable, preferably adapted for bearing in a defined position on the skin of a patient and for holding the puncture needle 2 during use. In the preferred embodiment which is shown, the holding device 1 comprises a housing 1a and two gripping wings 1b which can come into engagement with each other via an annular protrusion is and an annular groove 1d when the two gripping wings 1b are folded up. Preferably, the safety mechanism is blocked against getting triggered if the two gripping wings 1b are folded up. To this end, the two gripping wings 1b or even one of them may be formed with a stud or spike (not shown in further detail), for instance, which comes into (form-locking) engagement with the protection element 7 and arrests it in the first position.

The safety mechanism comprises the afore-mentioned protection element 7 which in the present case is formed like a sleeve, housing or clamp and can adopt a first, opened state (see FIG. 5) and a second, closed state (see FIGS. 2, 4 and 6). If the holding device 1 is taken away from the skin and/or moved with respect to the defined position, the safety mechanism automatically moves the protection element 7 from a first position in which the tip of the needle is exposed (see FIGS. 1, 3 and 5) to a second position in which the tip of the needle is covered (see FIGS. 2, 4 and 6). In this process, the protection element 7 at the same time transfers automatically from the first, opened state to the second, closed state.

In the preferred embodiment illustrated in FIGS. 1 to 6, this automatic safety mechanism is based on the fact that the safety mechanism 1 comprises a first spring 10 with which the protection element 7 can be moved from first position to the second position, and that the safety mechanism 1 comprises a second spring 12 which is suitable to automatically relax and thus release the first spring 10 when the holding device 1 is taken away from the skin and/or is moved with respect to the defined position. In the illustrated preferred embodiment, the first spring 10 is a coil spring whose proximal end rests against a connecting element 8 or is connected thereto (see FIGS. 5 and 6), whereas its distal end is connected to the proximal end of the protection element 7. If the protection element is in the first position, the coil spring 10 is compressed against its spring tension. Here, the protection element 7 is blocked in the first position as the second spring 12 comprises one or more latching hooks 12a engaging the first spring 10 in direct or indirect fashion. In the preferred embodiment which is shown here, the latching element 12a blocks the distal end of the protection element 7 and thus comes into engagement with the first spring 10 in indirect manner. In the case of the preferred embodiment illustrated here, the second spring 12 is a leaf spring which is pressed inwards (i.e. in upward direction in FIGS. 5 and 6) against its spring tension when the holding device rests on the skin of a patient. In case the holding device 1 releases from the skin of the patient, the second spring 12 may spring back from the housing 1a, as illustrated in FIGS. 4 and 6, so that the latching hook 12a releases the protection element 7 (and thus, in indirect fashion, the first spring 10). This allows the coil spring 10 to automatically expand so that its distal end moves the protection element 7 in distal direction to the second position in which the tip of the needle is covered (see FIGS. 2, 4 and 6).

The preferably hook-shaped latching element 12a might be triggered during transport in the package and/or during removing the protective cap of the needle 2 and/or during folding the wings 1b. It would likewise be disadvantageous if the mutual engagement between the latching element 12a and the protection element is so strong that the safety mechanism cannot be triggered in automatic or self-activating fashion. Accordingly, the protection element moving device, preferably the first spring and/or the latching element 12a itself have to be designed such that neither an unintentional unlocking process nor an undesired state of remaining locked occurs. Depending on the needle length, a different first and/or second spring, preferably another length and/or spring force are required, which are adapted to each other such that the resilient latching element 12a releases in self-acting manner, but can be secured for instance with a simple adhesive strip.

In the preferred embodiment illustrated here, the protection element 7 has two resilient arms which close the protection element 7 in the second state. In the first state, these two arms are kept spaced apart against their spring force due to the fact that the needle 2 is between the two arms (see FIG. 5). If the protection element 7 is moved by the spiral spring 10 from the first position to the second position, the arms of the protection element 7 slide along the outer side of the needle 2 until the distal end of the needle 7 is situated distally relative to the needle tip. As soon as the needle does not prevent the two arms from springing inwards any more, they spring toward each other and hence close the protection element 7.

In order to prevent the protection element 7 from detaching from the needle 2 or the coil spring 10 from moving the protection element 7 in distal direction beyond the needle tip, it is preferred that one or more protrusions 6 are provided on the distal end of the needle 2, with which the proximal end of the protection element 7 comes into engagement. As seen in axial direction, the two or more protrusions 6 are preferably arranged at the same position of the needle 2. As an alternative, the protrusions 6 are arranged at different positions of the needle 2 as seen in axial direction. It is preferred that the one or several protrusion(s) 6 is/are manufactured by a preferably mechanical crimping process.

The needle 2 is connected to the hose 5 via a connecting element 8, wherein the connecting element 8 is preferably rotatably supported in/on the housing 1a and preferably coupled to the housing 1a so as to be unable to be detached from it.

Figure 5A:
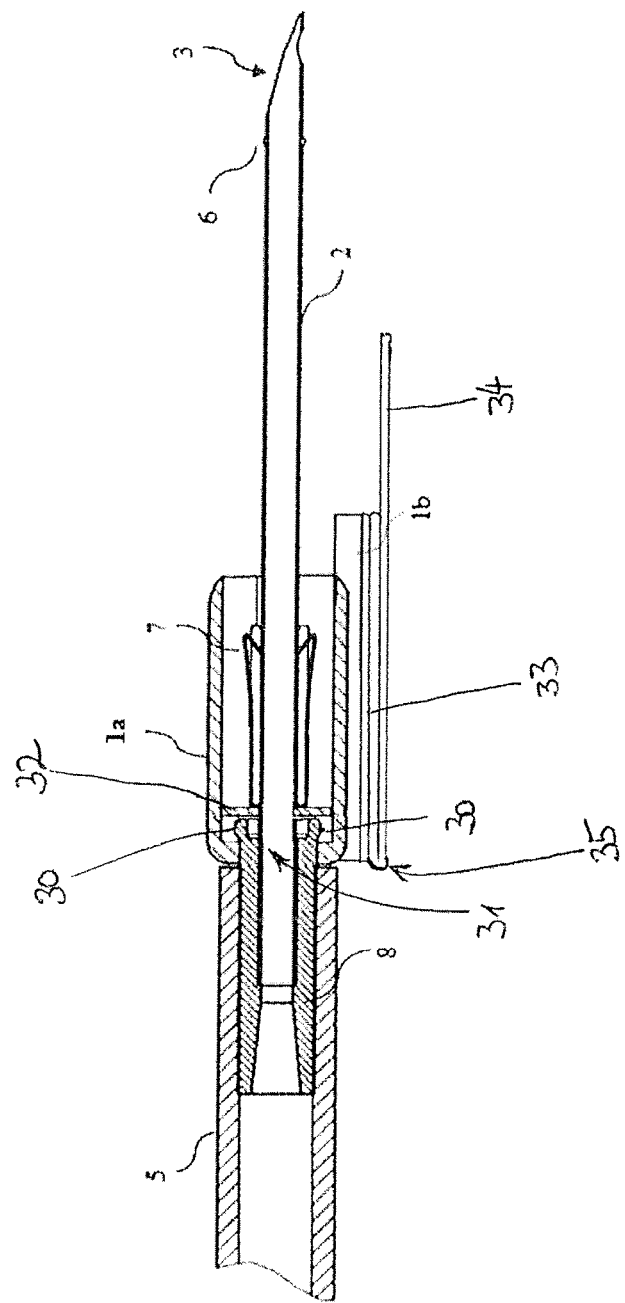
FIGS. 5A, 5B are lateral sectional views of the safety needle in alternative configurations in the first latching position.
Figure 6A:
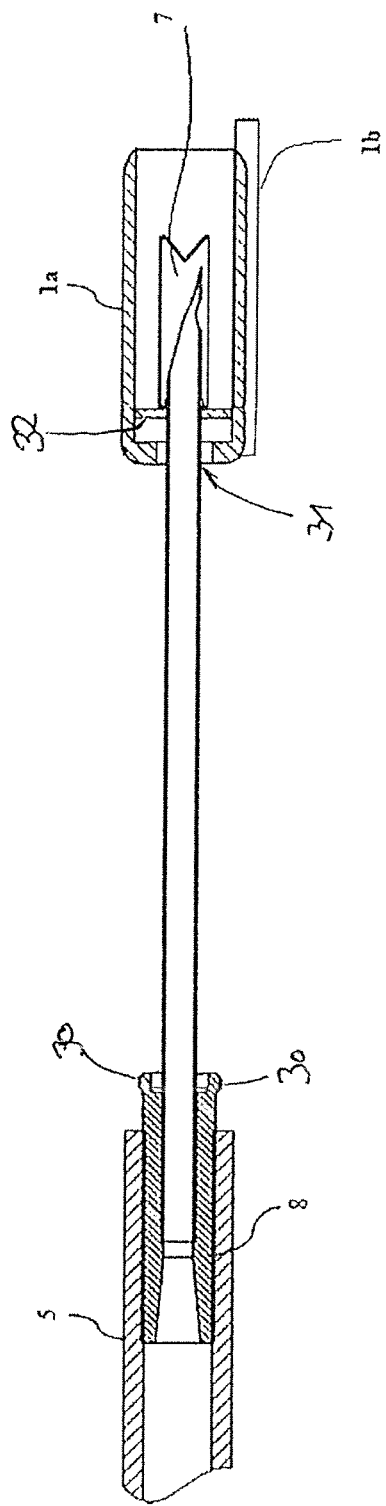
Figure 7:
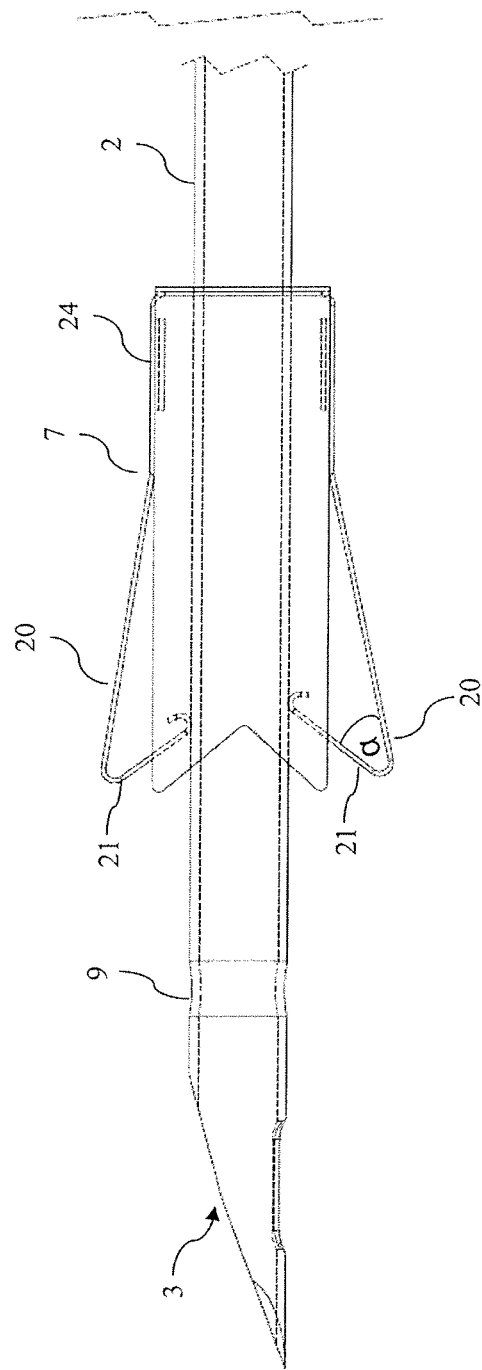
FIG. 7 is a lateral sectional view of a protection element according to a preferred embodiment in the first state.
Figure 8:
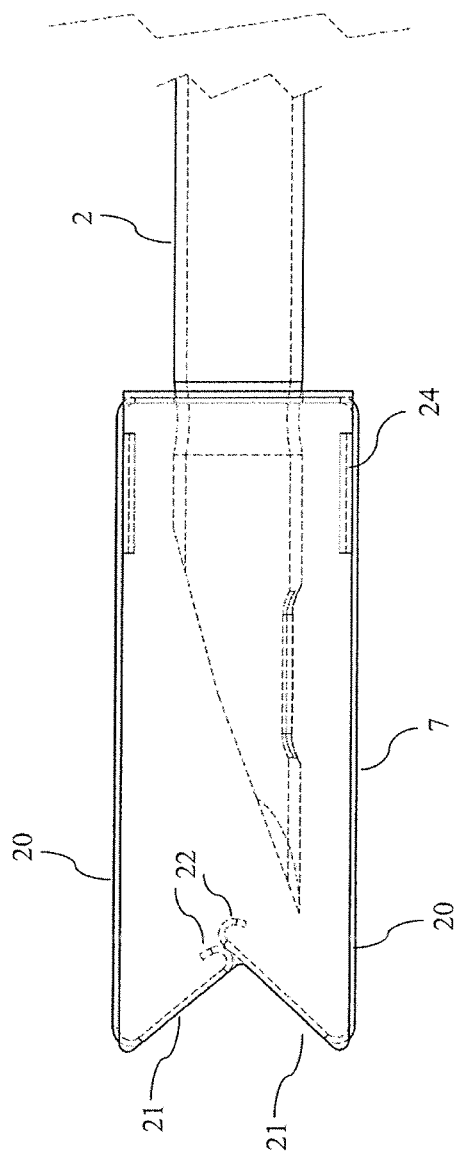
FIG. 8 is a lateral sectional view of the protection element according to FIG. 7 in the second state.

FIGS. 5A and 6A show a further embodiment of the present safety needle according to aspects of the invention. Identical elements and elements with the same function are designated with the same reference symbols, so that it is referred to the above description in this respect. According to the embodiment shown in FIGS. 5A and 6A, the connecting element 8 has its distal end provided with latching elements (e.g. latching tabs/ledge, etc.) 30 which have a larger spatial extension in the radial direction than the proximal opening 31 of the housing 1a. The latching elements have slots between them. The ratio between the size of the latching elements and the slots can be set so as to give a force required for unlatching a defined value. The latching elements 30 may also be formed as a latching ring. The opening 31 and the latching elements 30 of the connecting element 8 are designed such that the housing 1a and the connecting element 8 can be separated from each other as shown in FIG. 6A in the event of a proximal movement of the hose 5 or the connecting element 8 while having an unchanged position of the housing 1a with respect to the patient's skin. For separating the connecting element 8 and the housing 1a, the applied force must not be so high as would be required for removing the holding device 1, in particular via an adhesive layer 33, from the skin of a patient.

In addition, a retaining wall 32 or retaining ring 32 having an opening is provided proximally from the protection element 7 according to FIG. 5A, so that the needle 2 can be shifted in proximal direction, but the protection element 7 by the proximal movement of the needle 2 is shifted toward the tip 3 of the needle 2, i.e. in distal direction, and encompasses the tip 3 in the second position. The retaining wall 32 or retaining ring 32 (where the spring 10 is supported) is preferably made in one piece with the housing 1A. As an alternative, the retaining wall 32 or retaining ring 32 is preferably formed as a separate part. In that case, the retaining wall 32 or the retaining ring 32 is connected to the housing 1A with a retaining mechanism (clamping, latching, etc.). The safety needle according to FIG. 5A also comprises (in the area of contact between the holding device and the patient's skin) an adhesive layer 33 with which the holding device 1 can be placed/affixed on the skin of the patient. Prior to use and before positioning the safety needle at the correct place, this adhesive layer 33 is originally protected by a cover 34, also referred to as a cover layer, fully covering the adhesive layer 33 and having a fold portion 35 at the proximal end of the adhesive layer, so that the cover 34 can be peeled off in distal direction with a small distance between the holding device and the skin of the patient. The covering device 34 may also be applied onto the adhesive layer 33 such that it has the fold portion 35 at the distal end of the adhesive layer 33 and hence can be peeled off in proximal direction with a small distance between the holding device 1 and the skin of the patient. A corresponding adhesive layer 33 and covering device 34 are provided preferably with each safety needle according to aspects of the invention prior to attaching the safety needle to the patient.

Figure 5B:
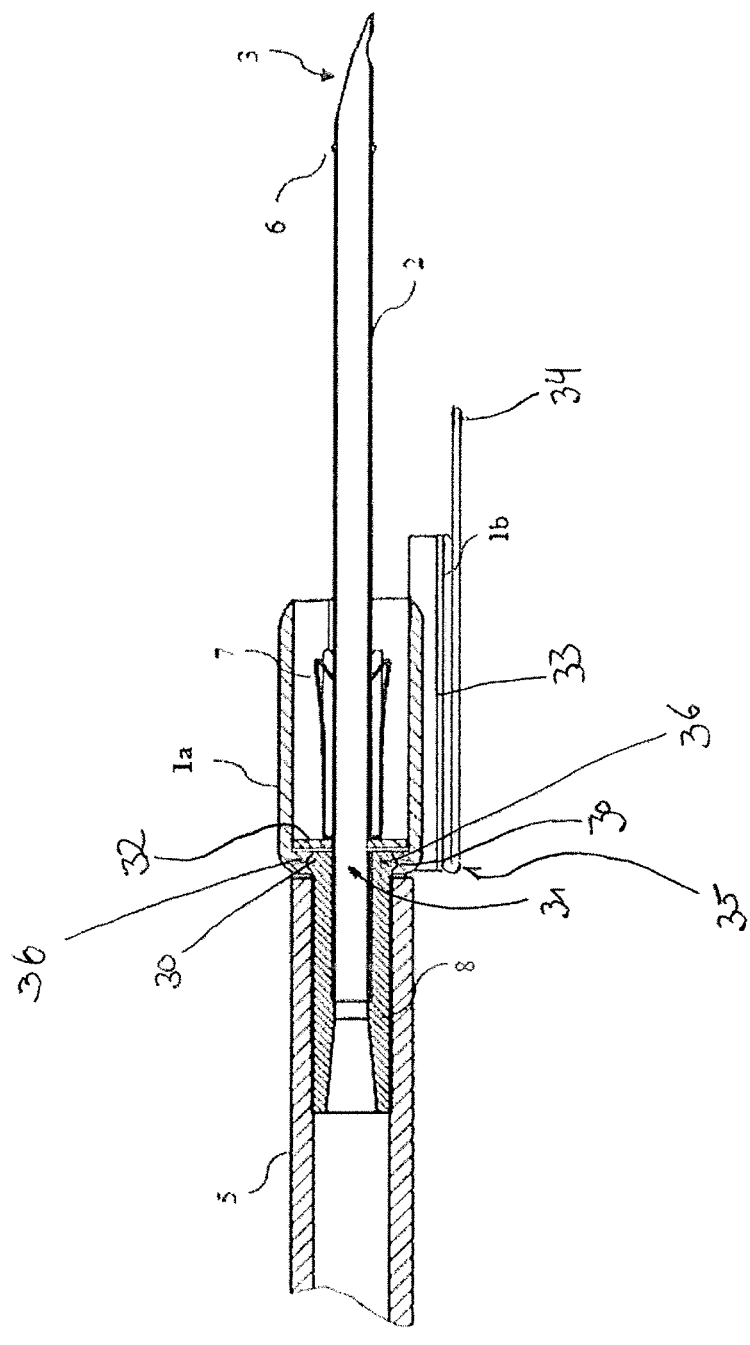

FIGS. 5B and 6B show a further embodiment of the present safety needle according to aspects of the invention. Identical elements and elements with the same function are designated with the same reference symbols, so that it is referred to the previous description in this respect. In this embodiment, the latching elements 30 preferably shaped in the form of a latching ring are latched in place in receiving elements 36 which are designed for receiving the latching elements 30, provided in the proximal wall of the housing 1a and realized preferably in the form of an annular groove. In comparison with the embodiment according to FIGS. 5A and 6A, the retaining wall 32 or retaining ring 32 is displaced in distal direction and rests flush against the proximal wall of the housing 1a.

FIGS. 7-11 show a preferred embodiment of the protection element 7 according to aspects of the invention. In the preferred embodiment illustrated here, the protection element 7 forms an essentially cuboid housing fully enclosing or enveloping the needle tip 3 in the closed state. The protection element 7 comprises a proximal wall portion 27 with an opening 26 for passing the needle 2, four lateral wall portions 20 and 23 as well as two distal wall portions 21. The lateral wall portions 20 are welded to the lateral wall portions 23 with tabs 24. The wall portions 20 may also be punched out in one piece with the remainder of the sheet metal. The two lateral wall portions 20 form two resilient arms whose distal ends are each provided with a distal wall portion 21. With the preferred embodiment illustrated here, which is formed from the punched metal sheet depicted in FIG. 9, the two distal wall portions 21 can be obtained in the usual manner as known in sheet metal working industry by bending or kinking the ends of the portions 20. In this arrangement, the portions 20 and 21 preferably form an acute angle α so that the distal wall portions 21 extend both inwards and in proximal direction starting from the distal end of the lateral wall portions 20. This promotes, among other things, that the protection element 7 slides along the outer side of the needle 2 with low friction. What is more, such an acute angle α is able to efficiently prevent the protection element 7 from being retracted from the second position illustrated in FIG. 8, as the bent section formed by the portions 20 and 21 would get entangled with the needle tip 3 in the event of such retraction. In order to account for this acute angle α and ensure a tight sealing of the protection element, the distal ends of the lateral wall portions 23 have corresponding triangular recesses, with the angle α illustrated in FIG. 9 corresponding to the angle α illustrated in FIG. 11. The angle α may also be larger than the angle α illustrated in FIG. 11 in order to bring about an overlap.

Figure 9:
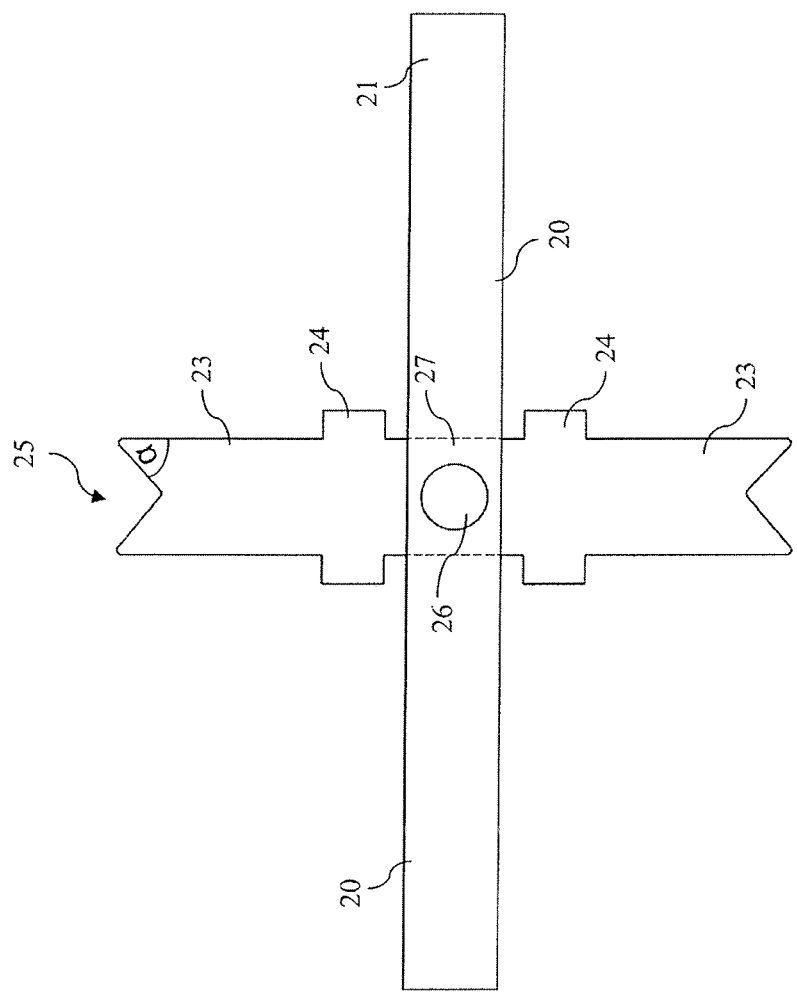
FIG. 9 is a top view of a punched metal foil from which a protection element according to aspects of the invention can be manufactured.
Figure 10:
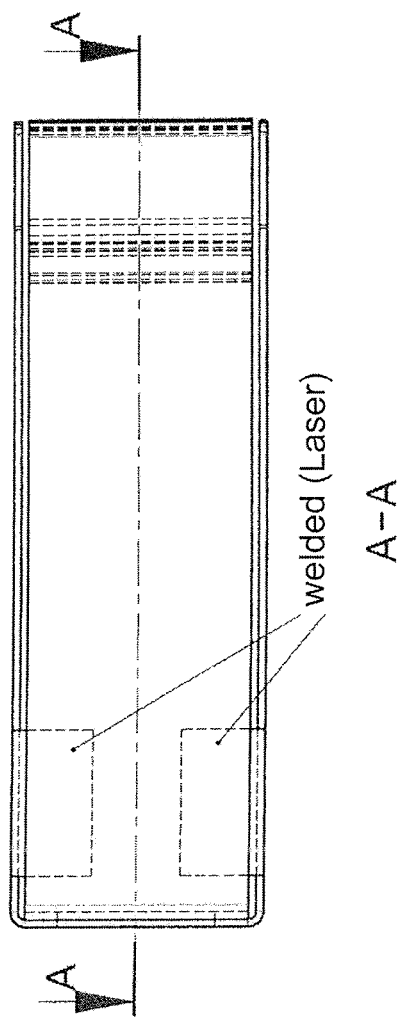
FIG. 10 is a partial sectional view, as seen from above, of a protection element according to a preferred embodiment.
Figure 11:
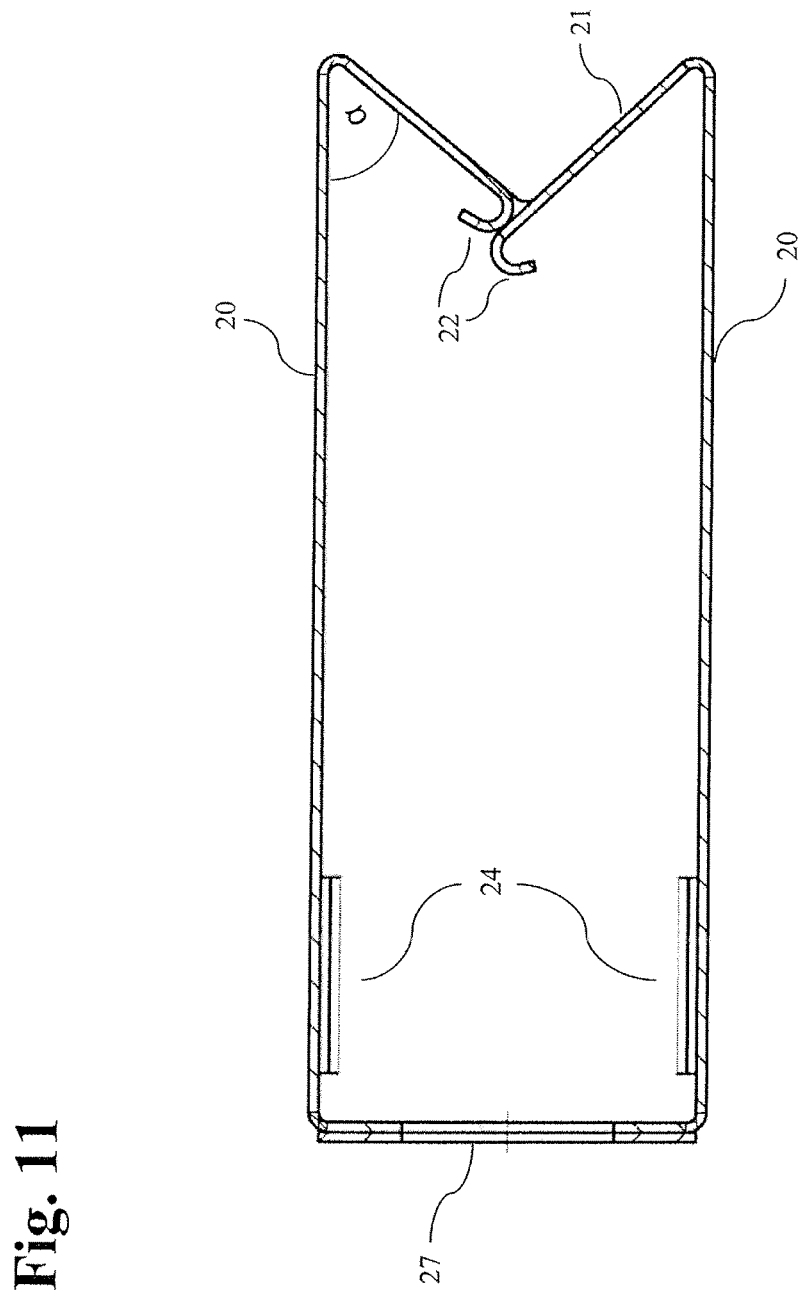
FIG. 11 is a lateral sectional view of the protection element according to FIG. 10.

As the protection element 7 is usually formed from a material (for instance a sheet metal with defined thickness), even the lateral wall portions 23 are generally elastic; however, this is not required because the wall portions 23 do not come into contact with the needle 2 during use. In order to give the lateral wall portions 20 a higher elasticity than the lateral wall portions 23, the former may have a smaller width than the latter, as can be seen in FIG. 9, for example. The elasticity may also be controlled via the wall thickness of the sheet metal. If another degree of elasticity is desired, a two-part construction such as illustrated in FIG. 9 is preferred. Preferentially, the side portions 23 have a lower elasticity than the wall portions 20. The elasticity may be influenced in particular by a curvature. Specifically, the elasticity may be brought about by an embossed curvature. This is advantageous if the side portions 23 are supposed to have a lower elasticity, preferably in connection with the one-piece construction. It is also possible to provide webs/ribs stiffening the side portions 23.

In cases where the angle α according to FIG. 9 is larger than the angle between the wall portions 20 and 21, a curvature of the side portions may also improve the sealing between the side portions 20, 21 and 23. The side portions 20 and 21 are pressed against the curved side portions 23 during closing.

The second, closed state of the protection element 7 is essentially effected in that the lateral wall portions 20, due to their inherent spring force, are pressed flush against the lateral wall portions 23. If metal edges meet metal edges, small gaps and/or openings 25 will be produced as a rule, which are unproblematic however as long as the flow resistance of human blood through all the gaps and/or openings is larger than the flow resistance through the needle lumen. The protection element 7 can be better closed or sealed, however, if the protection element 7 is made of an elastomer or coated with an elastomer at least in parts. It is especially preferred to provide an elastomer in the area of the edges or borders of the lateral wall portions 20 and 23 and/or distal wall portions 21. As seen from the viewpoint of manufacturing technology, however, it might be easier to fully coat the entire inner side of the protection element (i.e. the surface illustrated in FIG. 9) with an elastomer.

The distal wall portions 21 have their inner edges preferably provided with rounded zones and/or barbs 22. On the one hand, these rounded zones 22 reduce the sliding resistance with respect to the outer side of the needle 2 (see FIG. 7). On the other, these rounded zones may also serve as barbs 22 additionally securing the protection element 7 against a proximal retraction.

Figure 12:
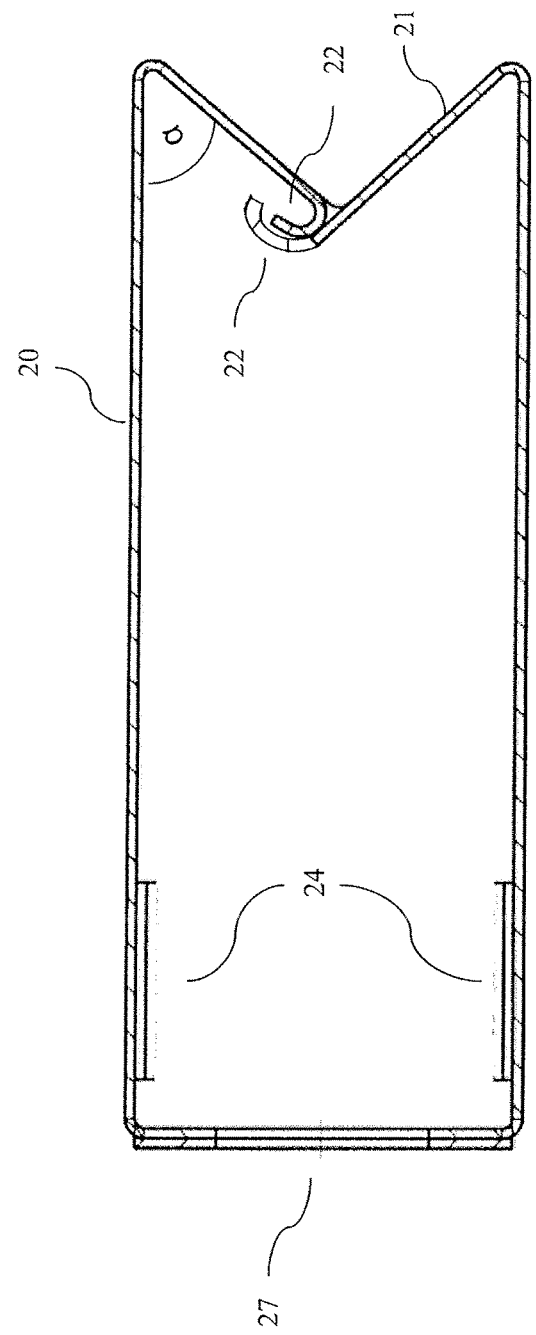
FIG. 12 is a lateral sectional view of a protection element according to a further preferred embodiment.

According to a further preferred embodiment schematically illustrated in FIG. 12, the barbs 22 may be formed such that they can get entangled with each other, so that the two arms 20 can engage each other if the protection element is in the second, closed position. To this end, the two barbs or rounded zones at the inner edges of the distal wall portions 21 may encompass or encircle each other, for instance, as can be seen in FIG. 12. This may prevent the two arms from being urged apart due to the pressure of the blood. However, the functions of preventing a retraction, on the one hand, and a pushing apart, on the other, do not have to be provided with the aid of the same elements 22. In addition to or instead of the barbs 22, the two arms may rather comprise other hook elements or curved zones which come into engagement or get entangled with each other in the second position.

FIG. 12A shows a protection element 7 comprising distal wall portions 21 which have their ends provided with bent portions 22, wherein the curvature of the two portions 22 is curved in the same direction. Varying the angle α and the curvature of the barb 22 allows to prevent an entangling of the wall portions 21 during assembling the needle with the protective device, on the one hand, and provide the largest possible resistance against the blood flowing out of the needle during use, on the other, so that the smallest possible amount of blood flows out of the safety device.

FIG. 13 shows a cross-section through FIG. 1. Identical elements and elements with the same function are designated with the same reference symbols, so that reference is made to the previous description in this respect. The two wings 1b have an annular protrusion 1c and an annular groove 1d which can come into engagement with each other.

At the underside of the holding device, an adhesive layer 33 can be seen which is covered by a cover layer 34 before positioning the needle on the skin of the patient. In comparison with FIGS. 5A and 5B, the cover layer 34 is not peeled off in axial direction, but in radial direction in the embodiment according to FIG. 13. The cover 34 covers the adhesive layer 33 preferably completely. The adhesive layer 33 may also cover the entire holding device 1. The cover 34 is preferably made in one piece. The cover may also be formed from two or more pieces, preferably in such a manner that each wing 1B has at least one cover 34 which can be peeled off in radially outward direction.

It goes without saying that the present invention is not limited to a protection element according to the preferred embodiment in FIGS. 7 to 11. The protection element does not have to be manufactured from a punched metal sheet, but may be made from plastic, for instance. Instead of two distal wall portions 21, it would also be possible to provide a single distal wall portion 21 having a correspondingly larger size and only provided at the distal end of a lateral wall portion 20. It is also not mandatory that the protection element has an essentially cuboid shape, but may also be a prism with a triangular, pentagonal or hexagonal base area, for example. As an alternative, the protection element may also have the shape of a circular cylinder and consist of two half shells, for instance. The lateral wall portions 20 and 23 do not have to be welded to each other, but may also be glued to each other, for example.

In general, other configurations of the protection element are also conceivable, and in this respect reference is made to the embodiments according to FIGS. 14A, 14B and 15A, 15B, for example, in which the needle may also be eccentrically arranged in the protection element (15A, 15B).

Figure 14:
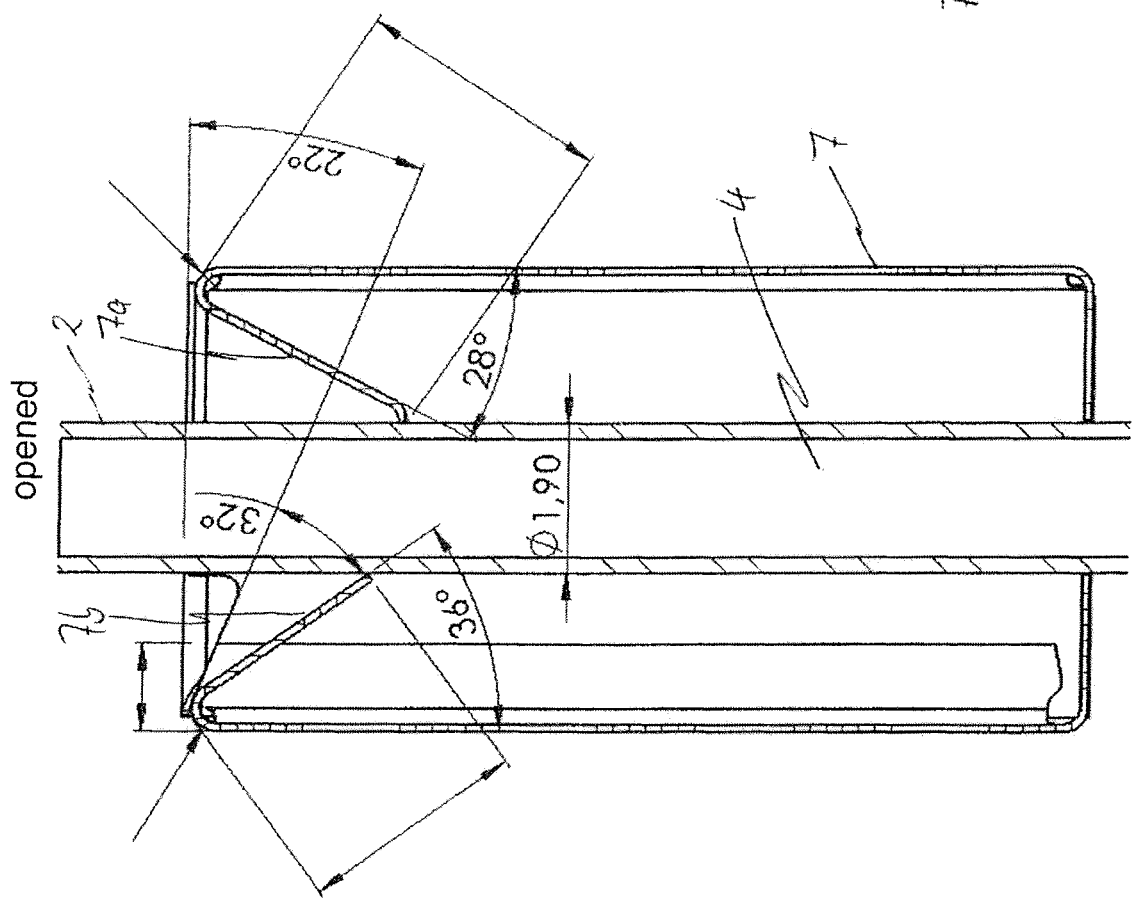
FIGS. 14A, 14B each show a lateral sectional view of a protection element according to a further preferred embodiment in the first and the second latching position.

Thus, the preferably housing-type or clamp-shaped protection element 7 according to FIG. 14A may have provided its distal end portion with two arms 7a, 7b that can pivot towards each other and have different arm lengths. This means that one arm 7b is shorter than the other arm 7a such that both arms 7a, 7b are swiveled apart by the inserted needle 2 by differing angles (e.g. 22° and 32° with respect to the vertical relative to the needle axis). As soon as the protection element 7 having the shorter arm 7b is pushed beyond the needle tip, this arm (first) swivels back to its closed position, while the longer arm 7a is spread apart (and kept spread apart) by the needle 2. As soon as the longer arm 7a has reached the needle tip and goes beyond it, it swivels back to its closed position as well and thus blocks the path for the needle 2 toward the surroundings in essentially tightening manner. This state is shown in FIG. 14B. In this respect, it is possible to fold the two arms into the closed position according to FIG. 14B in predetermined order and in this way reliably prevent the needle tip from piercing through.

In order to avoid the rebounding arms from an excessive pivoting movement, a pivoting stop/end stop (not shown in further detail) may be preferably provided against which the rebounding arms (swiveling into the closed position) may rest/strike.

Figure 15A:
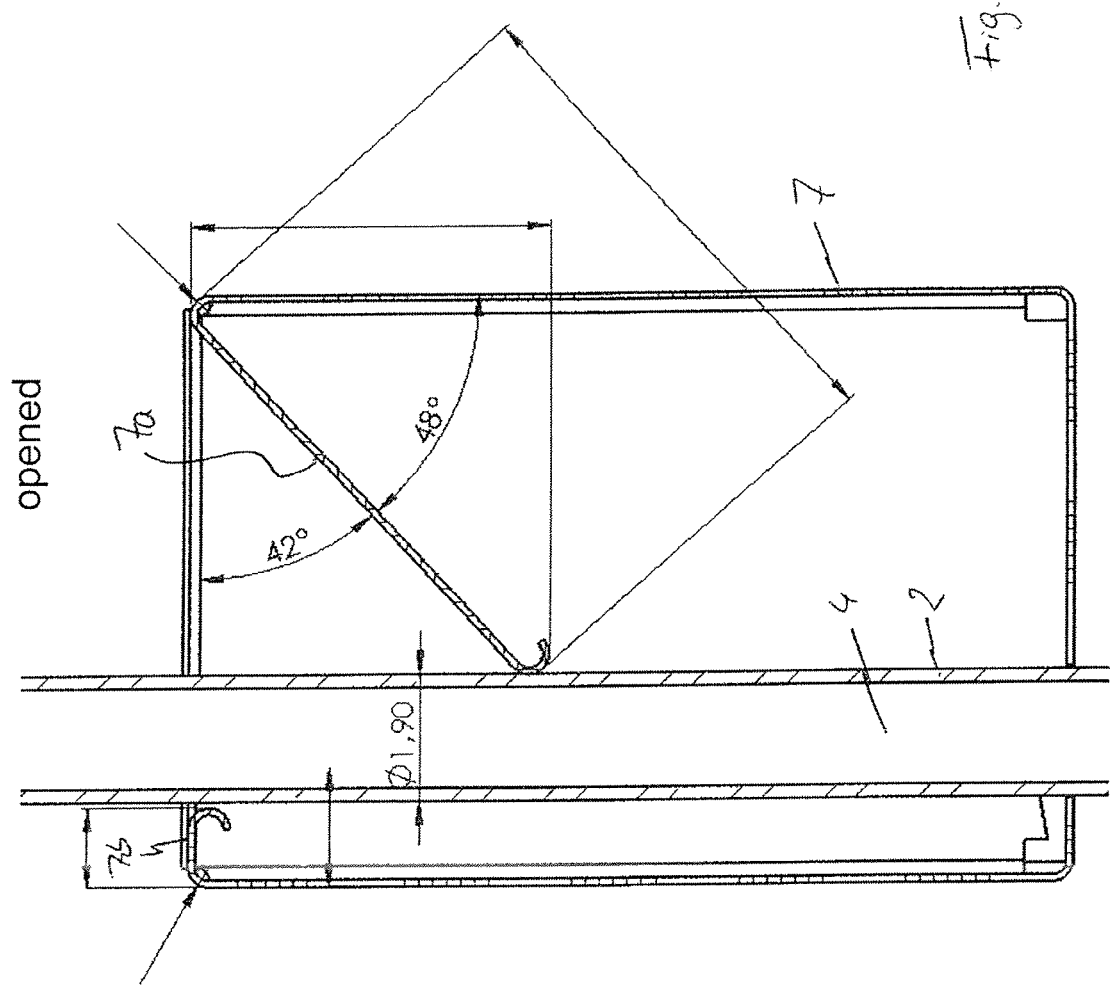

FIG. 15A illustrates an alternative to the configuration according to FIG. 14A.

According to this, the one (shorter) arm 7b is not pivotable (is rigid), whereas the other (longer) arm 7a is formed as it were so as to elastically swivel like a one-wing door such that it can be pivoted radially outwards by the needle 2. As soon as the protection element 7 is axially pushed beyond the needle tip, the one arm 7a swivels back to its sealing closed position according to FIG. 15B and encloses the needle tip within the protection element 7 preferably in sealing manner or largely sealing manner.

According to the preceding description, the design of the arms 7a, 7b on the protection element 7 is also supposed to provide a flow resistance for the blood emerging from the needle, producing a backpressure with a level which can be reliably detected by a suitable sensor system and ultimately results in powering down (and/or triggering an alarm) of the extracorporeal blood treatment machine.

Although basically possible, the still existing leakage of blood may have the effect that a certain time elapses until a sufficient backpressure has built up. In the meantime, a loss of blood has to be accepted.

In order to avoid this, a so-called blood stopping means (shut-off valve) may be disposed which can be provided in addition to or as an alternative to the sealing function of the protection element and hence shall be claimed in combination with the safety needle according to aspects of the invention or independently thereof. In this respect, the following description of the blood stopping means according to aspects of the invention is to be construed in combination with the previously described safety needle and also as a part separate therefrom. A blood stopping means according to aspects of the present invention generally has a housing 100 through which a flexible blood hose 102 extends. The housing 100 further mounts a clamping/pinching body 104 which is spring-biased against the blood hose 102. The clamping/pinching body 104 has an engagement edge/side 108 adapted to pinch off the blood hose 102 in an almost fluid-tight manner, the preload force of a preload spring 106 acting on the clamping/pinching body 104 being sufficient for this purpose.

The housing 100 supports a release button or release lever 110 which protrudes from the housing 100 or is mounted on an outer side of the housing and can be moved against the outer side of the housing or into the housing interior by the application of an external force. The release button or release lever 110 is in operative engagement with the clamping/pinching body 104 in such a manner that it restrains the latter in a first, not clamping/not squeezing position if it has been moved into/to the housing 100 and releases the clamping/pinching body 104 for its movement to a second, clamping or squeezing position if it moves out of/away from the housing 100.

If the housing 100 of the blood stopping means rests e.g. against the patient's skin—namely on the housing side where the release button/lever 110 is situated—the release button/lever 110 is pressed against/into the housing 100, with the clamping/pinching body 104 being held in the first position in which the blood can freely flow through the flexible hose 102 within the housing 100. On the contrary, if the housing 100 is lifted from the patient's skin, the release button/lever 110 springs out of/away from the housing 100 in a preferably spring-biased manner and releases the clamping/pinching body 104 such that the latter due to its spring preload is pressed against the flexible hose 102 situated in the housing 100 and blocks it.

FIG. 16 illustrates a first constructional embodiment of a blood stopping means according to aspects of the present invention.

Thus, the blood stopping means according to aspects of the invention comprises the housing 100 whose both sides are provided with patient's skin support pads 112 formed thereon, whose contact surfaces facing the patient's skin are provided with self-adhesive strips (not illustrated). The housing 100 forms a through-channel 114 in which the flexible (blood) hose 102 is placed or can be placed.

At the housing side facing the patient's skin, the release lever 110 is articulated on the housing 100, on which a latching pin 116 is formed/arranged which protrudes into the housing 100 and can be brought into latching engagement with the clamping body 104 which in the present case is supported in the housing like a rocker.

Specifically, a free end (facing away from the latching pin 116) of the rocker-type clamping body 104 is formed with a pinching edge 108 which is prestressed with the spring (coil spring) 106 against the through-channel 114 and the hose 102 placed therein. The other free end of the rocker-type clamping body 104 is formed with a latching means (e.g. in the form of a latching protrusion, but not illustrated in detail) which can be brought into a latching engagement with the latching pin 116 (e.g. in the form of a latching tab or hook) in order to hold the rocker-type clamping body 104 in the first position in which the pinching edge 108 is spaced from the through-channel 114 (from the flexible hose 102). The latching engagement is only possible if the release lever 110 has been swiveled against the corresponding housing side (and hence the latching pin 116 is pressed against the latching means).

Finally, a further actuation knob or button 118 is arranged/formed on the other free end of the rocker-type clamping body 104 (in the area of the latching means) and projects out of the housing 100 such that upon its manual operation the rocker-type clamping body 104 can be moved back from the second position, in which the pinching edge 108 is pressed against the inserted hose 102 with the spring 106, to the first position against the spring preload in which it can be brought into latching engagement with the release lever 110 or the latching pin 116 formed thereon.

The function of the blood stopping means according to aspects of the invention can be described as follows. At first, the housing 100 is affixed to the patient's skin, as a result of which the release lever 110 is pivoted toward the outer side of the housing (in a resilient manner—see the leaf spring according to FIG. 16 arranged on the trigger lever 110). As a next step, the rocker-type clamping body 104 is transferred by the actuation knob 118 to its first position in which it latches in place on the latching pin 116 at the release lever 110. Finally, the flexible hose 102 is pushed into the through-channel 114.

If the housing 100 of the blood stopping means is to be detached/lifted off from the patient's skin again, the release lever 110 swivels away from the housing side in resilient fashion, with the latching pin 116 joining in the pivoting movement and hence releasing the latching with the rocker-type clamping body 104. Due to the spring force acting on it, the latter is also pivoted by the spring 106 like a rocker, with its pinching edge 108 being pressed against the hose 102 and blocking it.

If the blood stopping means comprising the safety needle according to aspects of the invention is coupled preferably according to the previous description with the housing side (assembled or formed to result in a preferably rigid unit), releasing the safety needle from the patient's skin would quasi result in detaching the housing 100 of the blood stopping means from the patient's skin, as a result of which the previously described mechanism would be triggered (independently of the safety needle).

A constructionally different variant of the blood stopping means (shut-off valve) according to aspects of the invention is illustrated in FIG. 17.

Here too, a release lever 110 is articulated on the side of the housing 100 of the blood stopping means facing a patient's skin. In this case, however, the clamping body 104 is realized in the form of a spring-biased pin on one front side of which the preload spring 106 applies an axially oriented force and on the other front side of which the pinching edge 108 is formed.

In the portion of the pin 104 axially facing away from the spring 106, an engagement element 120 in the form of a holding rail is formed which is engaged by the release lever 110 in the manner of a toggle lever mechanism to shift the pin 104 to the first position (away from the through-channel 114 and the inserted flexible hose 102), when the release lever 110 is swiveled toward the housing side. In this respect, the function of the blood stopping means in the embodiment according to FIG. 17 corresponds to that of the exemplary embodiment according to FIG. 16 with the exception that the first position of the now pin-like clamping body 104 with the exemplary embodiment according to FIG. 17 is not latched in place, but has to be retained by the pivot position of the release levers 110 and the force continuously applied thereon.

Thus, the embodiment according to FIG. 17 is not necessarily meant to be a constructionally simpler variant of the embodiment according to FIG. 16. Rather, the aim is the effect that the mechanism does not have to be "armed" or "activated" as is the case with the embodiment according to FIG. 16.

Stated in other words, if the mechanism/the housing of the blood stopping means is bonded to the skin of a patient, the release lever 110 is brought closer to the housing 100 of the blood stopping means by force and hence the part/the engagement element 120 is moved into the housing 100 to unblock the blood route.

If the housing 100 is detached from the patient's skin, the spring 106 again moves the part/the engagement element 120 (out of the housing 100), so that no blood flow can occur. An alternative idea according to aspects of the invention may consist in that the aim is not to pinch off a hose, but to bring about the "displacement" of a housing segment which represents a part of the blood route and hence functions like the valve piston of a shut-off valve in slide valve design. It goes without saying that an appropriate sealing between the engagement element 120 and the housing 100 has to be provided here, so that the system works and no leaks occur.

A further alternative or additional way of implementing/arranging a blood stopping means is to design the housing of the holding device with a so-called duckbill valve which shall be claimed also in combination with the safety needle according to aspects of the invention or independently thereof.

Such a valve is schematically illustrated in FIGS. 17A and 17B, for example. In this case, the housing 1a, as already described above on the basis of FIGS. 1 to 13, is formed or provided with a sort of everting collar 200 (duckbill valve) which is arranged at the distal front edge of the housing 1a and has a function similar to that of the pivotable arms on the protection element 7.

Figure 18A:
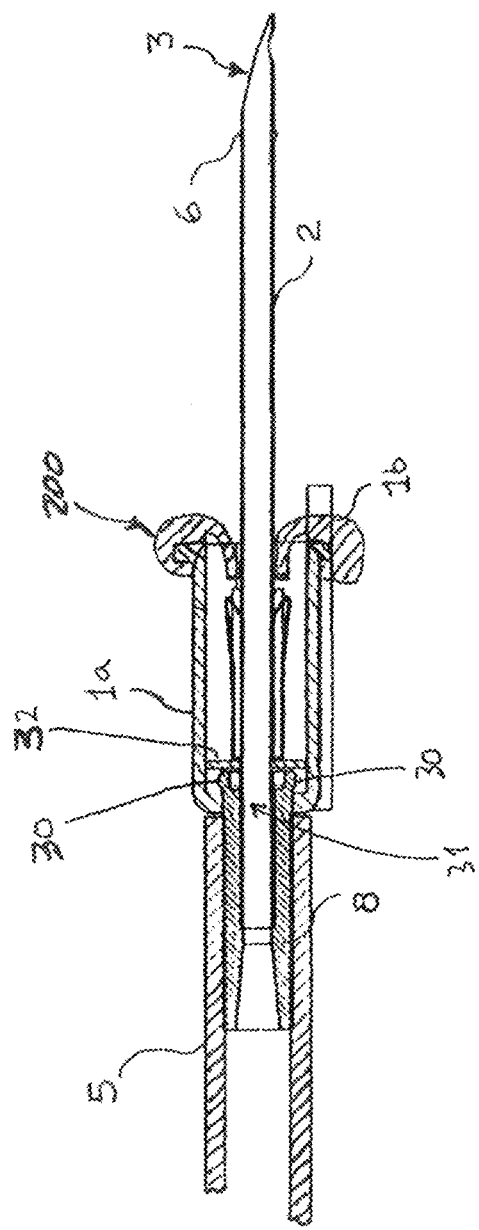
Figure 18B:
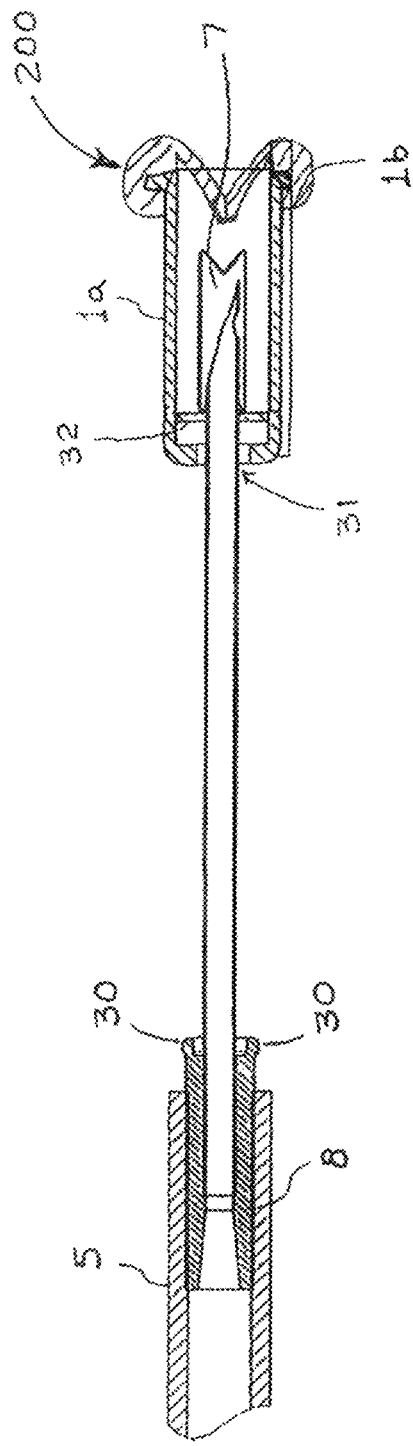

In the present case, the everting collar 200 is placed on the distal end portion of the housing of the holding device and closes the housing in a resilient fashion in distal direction. The puncture needle can now be pushed through the everting collar 200 by radially spreading it apart. This state is illustrated in FIG. 18A.

If the puncture needle 2 is to be retracted into the housing of the holding device (the protection element 7 has already been actuated and closes the tip of the puncture needle 2), the everting collar closes the housing and in this way largely prevents a leakage of blood.

The invention claimed is:

1. A safety needle comprising:
   a puncture needle having a needle lumen and a tip;
   a holding device that, during use, bears on skin of a patient and holds the puncture needle; and
   a safety mechanism with a protection element movably mounted to the holding device and configurable in a first, opened state and a second, closed state, wherein:
     the safety mechanism is configured to move the protection element from a first position, in which the tip of the puncture needle is exposed, to a second position, in which the tip of the puncture needle is covered, when the protection element at the same time transfers from the first, opened state to the second, closed state,
     the protection element comprises at least one of gaps or openings in the second state and a flow resistance of human blood through all of the at least one of gaps or openings is larger than a flow resistance of human blood through the needle lumen, and
   wherein the holding device comprises or forms a housing for receiving the entire protection element therein, the holding device has an opening in a distal direction so as to allow a movement of the protection element out of the housing and toward the needle tip, the opening elastically closed by an everting collar.

2. The safety needle according to claim 1, wherein the safety mechanism comprises a first spring configured to move the protection element from the first position to the second position.

3. The safety needle according to claim 2, wherein the safety mechanism comprises a second spring which, when the holding device is at least one of taken away from the skin or moved with respect to a defined position, is configured to relax automatically to release the first spring.

4. The safety needle according to claim 3, wherein the second spring at least one of (1) is a leaf spring or a conical coil spring or (2) comprises one or more latching hooks entering into engagement with the first spring in a direct or indirect manner.

5. The safety needle according to claim 1, wherein the flow resistance of human blood through all of the at least one of gaps or openings is larger than the flow resistance through the needle lumen by such an amount that maintaining a constant blood flow of between 300 ml/min and 600 ml/min requires a pressure increase of at least 10 mmHg.

6. The safety needle according to claim 1, wherein the flow resistance of human blood through all of the at least one of gaps or openings is larger than the flow resistance through the needle lumen by such an amount that maintaining a constant blood flow of between 300 ml/min and 600 ml/min requires a pressure increase of at least 30 mmHg.

7. The safety needle according to claim 1, wherein the flow resistance of human blood through all of the at least one of gaps or openings is larger than the flow resistance through the needle lumen by such an amount that maintaining a constant blood flow of between 300 ml/min and 600 ml/min requires a pressure increase of at least 50 mmHg.

8. The safety needle according to claim 1, wherein a sum of a respective cross-sectional area of all of the at least one of gaps or openings is smaller than a cross-sectional area of the needle lumen.

9. The safety needle according to claim 1, wherein the protection element comprises two resilient arms configured to close the protection element in the second state.

10. The safety needle according to claim 9, wherein the two resilient arms are formed such that in the first state they are able to slide along an outer side of the needle with low friction.

11. The safety needle according to claim 9, wherein at least one of the two resilient arms has its distal end provided with an arresting device that prevents the protection element from being moved from the second position to the first position.

12. The safety needle according to claim 11, wherein the arresting device comprises at least one of a bent portion of the at least one arm or a barb.

13. The safety needle according to claim 12, wherein the two resilient arms are configured to come into engagement with each other if the protection element is in the second position.

14. The safety needle according to claim 13, wherein the two resilient arms are configured to at least one of interlock with each other or get entangled with each other if the protection element is in the second position.

15. The safety needle according to claim 1, wherein a distal end of the protection element has a concave design.

16. The safety needle according to claim 1, wherein the protection element is made of an elastomer or coated with an elastomer at least in parts.

17. The safety needle according to claim 16, wherein the elastomer comprises one or more of the following materials: silicone, polyurethane, PTFE.

18. The safety needle according to claim 1, wherein an inner side of the protection element is coated at least in parts with a coagulatory material.

19. The safety needle according to claim 18 wherein the coagulatory material comprises one or more of the following materials: proteins; polypeptides;
polysaccharides; glucosamines; alginates; adsorbing substances; and/or denaturing substances.

20. The safety needle according to claim 1, wherein the protection element has an inner side provided with one or more of the following materials: elastic foamed plastic; swelling agents; spongy and/or water-absorbing substances.

21. The safety needle according to claim 1, wherein the needle comprises one or more protrusions preventing the protection element from detaching from the needle.

22. The safety needle according to claim 1, further comprising a connecting element connecting the protection element to a needle attachment of the needle.

23. The safety needle according to claim 1, wherein the holding device is provided with at least one of an adhesive strip, a detachable clip or a hand grip to prevent the safety mechanism from being activated before use of the safety needle.

24. A safety needle comprising:
a puncture needle having a needle lumen and a tip;
a holding device that, during use, bears on skin of a patient and holds the puncture needle;
a blood stopping means comprising a clamping/pinching body which is biased against a flexible hose and at least one of a release lever or release button which is in operative engagement or can be brought into operative engagement with the clamping/pinching body, said at least one of the release lever or release button being connected to the holding device such that during/by applying the holding device on a surface the at least one release lever or release button is moved to a first flow position in which the at least one release lever or release button keeps the clamping/pinching body spaced from the hose and during lifting the holding device from the surface automatically moves to a second flow position in which the clamping/pinching body pinches off the flexible hose; and
a safety mechanism with a protection element movably mounted to the holding device and configurable in a first, opened state and a second, closed state, wherein:
the safety mechanism is configured to move the protection element from a first position, in which the tip of the puncture needle is exposed, to a second position, in which the tip of the puncture needle is covered, when the protection element at the same time transfers from the first, opened state to the second, closed state, and
the protection element comprises at least one of gaps or openings in the second state and a flow resistance of human blood through all of the at least one of gaps or openings is larger than a flow resistance of human blood through the needle lumen.

\* \* \* \* \*